(12) United States Patent
Furutani et al.

(10) Patent No.: US 9,695,447 B2
(45) Date of Patent: Jul. 4, 2017

(54) RECOMBINANT CELL AND METHOD FOR PRODUCING ISOPRENE

(71) Applicant: SEKISUI CHEMICAL CO., LTD., Osaka (JP)

(72) Inventors: Masahiro Furutani, Tokyo (JP); Akihiro Uenishi, Tsukuba (JP); Koichiro Iwasa, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/655,934

(22) PCT Filed: Dec. 26, 2013

(86) PCT No.: PCT/JP2013/084915
§ 371 (c)(1),
(2) Date: Jun. 26, 2015

(87) PCT Pub. No.: WO2014/104202
PCT Pub. Date: Jul. 3, 2014

(65) Prior Publication Data
US 2015/0337338 A1    Nov. 26, 2015

(30) Foreign Application Priority Data

Dec. 27, 2012 (JP) ................ 2012-285055

(51) Int. Cl.
| | | |
|---|---|---|
| *C12P 5/02* | (2006.01) | |
| *C12N 1/20* | (2006.01) | |
| *C12N 1/00* | (2006.01) | |
| *C07H 21/04* | (2006.01) | |
| *C12N 9/90* | (2006.01) | |
| *C12N 9/88* | (2006.01) | |
| *C12P 5/00* | (2006.01) | |
| *C12N 15/52* | (2006.01) | |

(52) U.S. Cl.
CPC ........... *C12P 5/026* (2013.01); *C12N 9/88* (2013.01); *C12N 9/90* (2013.01); *C12N 15/52* (2013.01); *C12P 5/007* (2013.01); *C12Y 401/02043* (2013.01); *C12Y 402/03027* (2013.01); *C12Y 503/01027* (2013.01); *C12Y 503/03002* (2013.01); *Y02E 50/343* (2013.01)

(58) Field of Classification Search
None
See application file for complete search history.

(56) References Cited

U.S. PATENT DOCUMENTS

| | | |
|---|---|---|
| 2009/0203102 A1 | 8/2009 | Cervin et al. |
| 2015/0284742 A1 | 10/2015 | Furutani et al. |
| 2015/0315599 A1* | 11/2015 | Shetty .............. C12N 15/52 435/6.18 |

FOREIGN PATENT DOCUMENTS

| | | |
|---|---|---|
| JP | 2008-35831 | 2/2008 |
| WO | 02/18617 | 3/2002 |
| WO | 2009/076676 | 6/2009 |
| WO | 2009/132220 | 10/2009 |
| WO | 2010/031068 | 3/2010 |
| WO | 2013/110797 | 8/2013 |

OTHER PUBLICATIONS

International Preliminary Report on Patentability issued Jul. 9, 2015 in International Application No. PCT/JP2013/084915.
Supplementary European Search Report issued May 23, 2016 in European patent application No. 13 86 9129.
International Search Report issued Feb. 25, 2014 in International (PCT) Application No. PCT/JP2013/084915.
Yang, J. et al., "Bio-Isoprene Production Using Exogenous MVA Pathway and Isoprene Synthase in *Escherichia coli*", Bioresource Technology, Jan. 2012, vol. 104, pp. 642-647.
Zhao, Y., "Biosynthesis of Isoprene in *Escherichia coli* Via Methylerythritol Phosphare (MEP) Pathway", Appl. Microbiol Biotechnol., 2011, vol. 90, pp. 1915-1922.
Yang, J. et al., Enhancing Production of Bio-Isoprene Using Hybrid MVA Pathway and Isoprene Synthase in *E. coli*, PLoS One 2012, 7 (4).

* cited by examiner

*Primary Examiner* — Iqbal H Chowdhury
(74) *Attorney, Agent, or Firm* — Wenderoth, Lind & Ponack, L.L.P.

(57) ABSTRACT

An object of the present invention is to provide a series of techniques for producing isoprene from methanol or the like. Provided is a recombinant cell prepared by introducing a gene encoding isoprene synthase, into a host cell which is a methylotroph, wherein the gene is expressed in the host cell, and the recombinant cell is capable of producing isoprene from at least one C1 compound selected from the group consisting of methane, methanol, methylamine, formic acid, formaldehyde, and formamide. Preferably, it has at least one C1 carbon assimilating pathway selected from the group consisting of a serine pathway, a ribulose monophosphate pathway, and a xylulose monophosphate pathway as a fixing pathway of formaldehyde. Also provided is a method for producing isoprene using the recombinant cell.

7 Claims, 1 Drawing Sheet

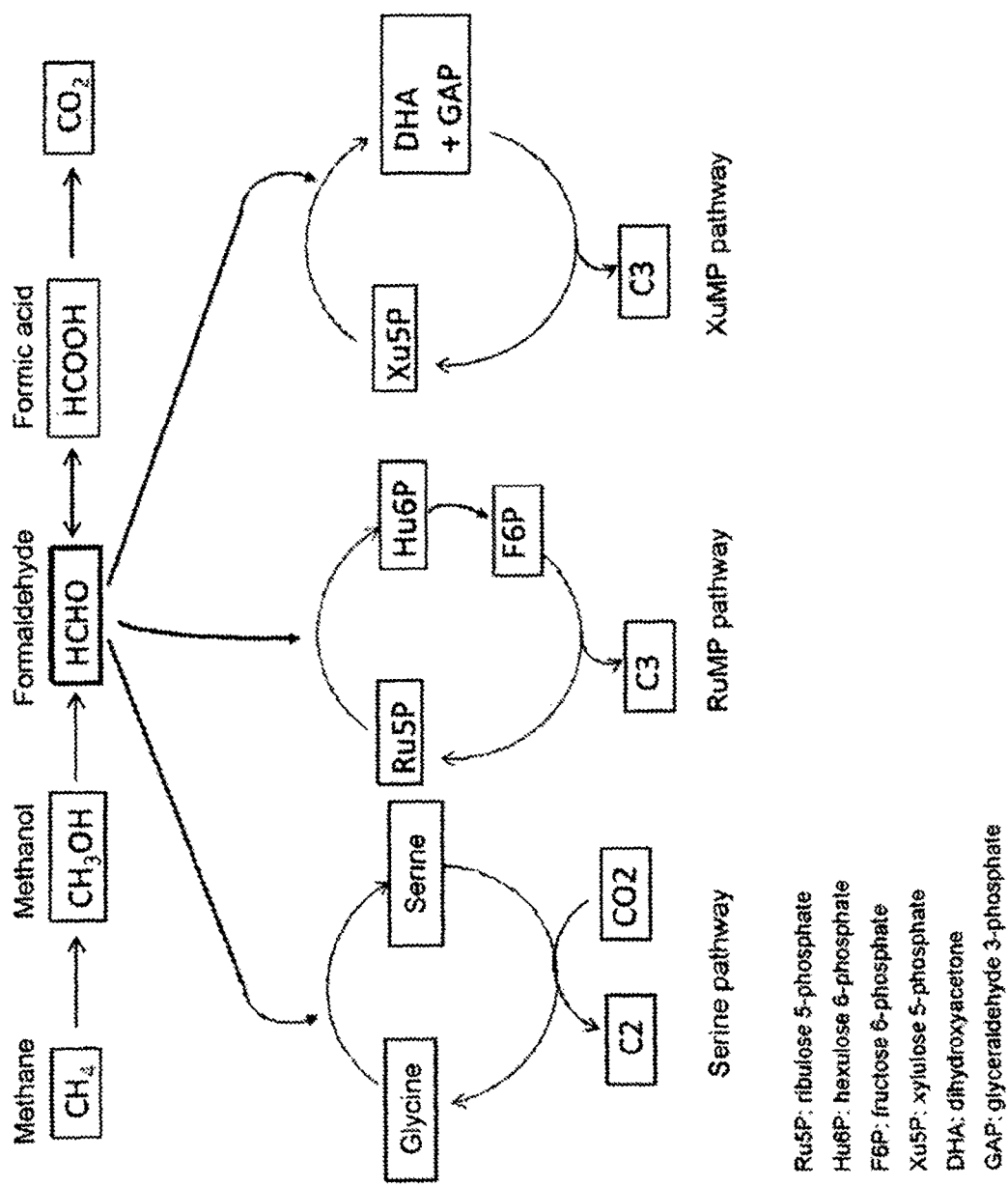

RECOMBINANT CELL AND METHOD FOR PRODUCING ISOPRENE

TECHNICAL FIELD

The present invention relates to a recombinant cell capable of producing isoprene from methanol or the like, and a method for producing isoprene using the recombinant cell.

BACKGROUND ART

Isoprene is a monomer raw material for synthetic polyisoprene, and is an important material, in particular, in the tire industry. In recent years, the technique for conversion from a production process of basic chemicals relying on petroleum to a production process from renewable resources such as plant resources has been developed and practical realization thereof is steadily progressing. Also regarding isoprene, for example, a production technique from saccharides as a raw material by recombinant *Escherichia coli* is known (Patent Documents 1 and 2, and Non-patent Document 1).

On the other hand, among C1 compounds, methanol is produced at a low cost from natural gas, synthetic gas which is a mixed gas of carbon monooxide, carbon dioxide and hydrogen obtained from biomass and wastes such as municipal wastes, and so on. Natural gas is focused as a next-generation energy source because it abundantly exists in fossil resources, and generates a relatively small amount of $CO_2$, and transition from conventional petroleum to natural gas is progressing. Methanol is easy to handle and stock because of its water solubility and so on, and is also suited as a carbon source in microbial culture.

A methylotroph is a general name for a C1 compound assimilating microorganism that uses a carbon compound not having a C—C bond in the molecule, e.g., methane, methanol, methylamine, dimethylamine, trimethylamine or the like as a sole carbon source or energy source. Any microorganisms called methanotroph, methane-oxidizing bacteria, methanol assimilating bacteria, methanol assimilating yeast, methanol assimilating microorganism belong to methylotrophs.

Central metabolism of methylotroph is a reaction of converting formaldehyde into an organic matter having a C—C bond after converting methanol to formaldehyde. As shown in the FIGURE, as a carbon assimilation metabolism pathway via formaldehyde, a serine pathway, a ribulose monophosphate pathway (RuMP pathway), and a xylulose monophosphate pathway (XuMP pathway) can be recited. Methylotrophs classified into bacteria (methylotrophic bacteria) have a serine pathway or a RUMP pathway. On the other hand, methylotrophs classified into yeast (methylotrophic yeast) has a XuMP pathway.

Methylotrophic bacteria are classified into obligate methylotrophs and facultative methylotrophs capable of using other carbon compound according to the difference in methanol requirement.

PRIOR ART DOCUMENTS

Patent Document

Patent Document 1: WO 2009/076676
Patent Document 2: WO 2009/132220

Non-Patent Document

Non-patent Document 1: Yang J., et al., PLoSOne 2012, 7(4), e33509

DISCLOSURE OF INVENTION

Technical Problem

Regarding the production process from renewable resources, most of the conventional techniques including the aforementioned isoprene production technique are production methods by microorganisms relying on organic substances, in particular, saccharides, glycerol or oil components. However, for covering the global production quantity of a large number of basic chemicals derived from petroleum, the amounts of currently available saccharides, glycerin and oil components derived from plant resources and the like will be necessarily insufficient for carbon sources of microorganisms. In other words, the production amounts of basic chemicals by microorganisms relying on saccharides or oil components is limited also in the future. These processes also have a fear of competition with foods.

Application examples of methylotrophs include production techniques of SCP (single cell protein), biodegradable plastic, amino acid and so on from methanol. However, there has been no case that a methylotroph is applied to production of basic chemicals derived from petroleum such as isoprene. As described above, all of the monomer compounds utilized in general polymer material products rely on petroleum at present, however, the possibility that petroleum having the quality equivalent to that of currently used petroleum is supplied is very low, and development of a new, efficient, alternative process is urgently demanded. Although a technique of saccharifying hard biomass including cellulose, hemicellulose, lignin and the like is examined for the purpose of ensuring carbon sources for production of chemicals by microorganisms, an enzyme treatment for saccharification is required, and a significant problem in terms of the cost arises.

In light of the above, it is an object of the present invention to provide a series of techniques capable of producing isoprene from methanol or the like.

Solution to Problem

One aspect of the present invention for solving the aforementioned problem is a recombinant cell prepared by introducing a gene encoding isoprene synthase, into a host cell which is a methylotroph, wherein the gene is expressed in the host cell, and the recombinant cell is capable of producing isoprene from at least one C1 compound selected from the group consisting of methane, methanol, methylamine, formic acid, formaldehyde, and formamide.

Isoprene synthase has the function of converting dimethylallyl diphosphate (DMAPP) which is an isomer of isopentenyl diphosphate (IPP) into isoprene. Structure conversion between isopentenyl diphosphate and dimethylallyl diphosphate is catalyzed by isopentenyl diphosphate isomerase. Isopentenyl diphosphate isomerase exists in any organism.

The recombinant cell of the present aspect is prepared by introducing a gene encoding isoprene synthase, into a host cell which is a methylotroph, and the gene is expressed in the host cell. And it is able to produce isoprene from at least one C1 compound selected from the group consisting of methane, methanol, methylamine, formic acid, formaldehyde, and formamide. The recombinant cell of the present aspect is able to convert dimethylallyl diphosphate and isopentenyl diphosphate synthesized in the cell into isoprene by the action of isoprene synthase. That is, according to the recombinant cell of the present aspect, it is possible to produce isoprene from the aforementioned C1 compound.

Preferably, the recombinant cell has at least one C1 carbon assimilating pathway selected from the group consisting of a serine pathway, a ribulose monophosphate pathway, and a xylulose monophosphate pathway as a fixing pathway of formaldehyde.

Preferably, a gene encoding 3-hexulose-6-phosphate synthase and a gene encoding 6-phospho-3-hexuloisomerase are further introduced, and the genes are expressed in the host cell.

With such a configuration, formaldehyde fixing ability by the ribulose monophosphate pathway is imparted or enhanced.

Preferably, the host cell is bacterium or yeast.

Preferably, the yeast belongs to genus *Pichia*, genus *Hansenula*, or genus *Candida*.

Other aspect of the present invention for solving a similar problem is a recombinant cell prepared by introducing a gene imparting the function of converting methanol and/or formic acid into formaldehyde, a gene imparting formaldehyde fixing ability, and a gene encoding isoprene synthase, into a host cell, wherein the genes are expressed in the host cell, and the recombinant cell is capable of producing isoprene from at least one C1 compound selected from the group consisting of methane, methanol, methylamine, formic acid, formaldehyde, and formamide.

The recombinant cell of the present aspect is prepared by introducing "gene imparting the function of converting methanol and/or formic acid into formaldehyde", "gene imparting formaldehyde fixing ability", and "gene encoding isoprene synthase" into a host cell, and these genes are expressed in the host cell. And it is able to produce isoprene from at least one C1 compound selected from the group consisting of methane, methanol, methylamine, formic acid, formaldehyde, and formamide.

That is, since the recombinant cell of the present aspect is prepared by introducing "gene imparting the function of converting methanol and/or formic acid into formaldehyde", and "gene imparting formaldehyde fixing ability", it has characteristics similar to those of a methylotroph. And, since "gene encoding isoprene synthase" is introduced, isoprene synthase can be expressed in the cell. As a result, it is possible to convert isopentenyl diphosphate synthesized in the cell into isoprene. That is, also by the recombinant cell of the present aspect, it is possible to produce isoprene from the aforementioned C1 compound.

Preferably, the recombinant cell has at least one C1 carbon assimilating pathway selected from the group consisting of a serine pathway, a ribulose monophosphate pathway, and a xylulose monophosphate pathway as a fixing pathway of formaldehyde.

Another aspect of the present invention for solving a similar problem is a recombinant cell prepared by introducing a gene imparting the function of converting methanol and/or formic acid into formaldehyde and a gene encoding isoprene synthase, into a host cell having a ribulose monophosphate pathway, wherein the genes are expressed in the host cell, and the recombinant cell is capable of producing isoprene from at least one C1 compound selected from the group consisting of methane, methanol, methylamine, formic acid, formaldehyde, and formamide.

The present aspect corresponds to the form wherein, for example, a non-methylotroph having a ribulose monophosphate pathway is a host cell.

Preferably, the gene imparting the function of converting methanol into formaldehyde is a gene encoding methanol dehydrogenase or alcohol oxydase, and the gene imparting the function of converting formic acid into formaldehyde is a gene encoding formaldehyde dehydrogenase.

Both of methanol dehydrogenase and alcohol dehydrogenase have the function of converting methanol into formaldehyde. Also, formaldehyde dehydrogenase has the function of converting formic acid into formaldehyde. Any of these enzymes is one of the methane metabolism enzymes in methylotrophs belonging to bacteria. On the other hand, methylotrophs belonging to yeast does not have methane oxidizing activity, but has the function of converting methanol into formaldehyde by the action of alcohol oxydase. Also yeast has the enzymatic activity of converting formic acid into formaldehyde.

Preferably, a gene imparting the function of converting methane into methanol is further introduced, and the gene is expressed in the host cell.

Preferably, the gene imparting the function of converting methane into methanol is a gene encoding methane monooxygenase.

Methane monooxygenase has the function of converting methane into methanol. Also methane monooxygenase is one of methane metabolism enzymes in methylotrophs.

Preferably, a gene encoding 3-hexulose-6-phosphate synthase and a gene encoding 6-phospho-3-hexuloisomerase are further introduced, and the genes are expressed in the host cell.

Preferably, the host cell is bacterium or yeast.

Preferably, the host cell has isopentenyl diphosphate synthesis ability by a mevalonate pathway, and a gene encoding at least one enzyme acting in a mevalonate pathway and/or a gene encoding a group of enzymes acting in a non-mevalonate pathway are/is further introduced, and the gene is expressed in the host cell.

With such a configuration, synthesis ability of IPP which is a supply source of DMAPP is enhanced, and IPP and DMAPP are efficiently supplied. As a result, the recombinant cell of the present aspect has still higher isoprene productivity.

Preferably, the gene encoding at least one enzyme acting in a mevalonate pathway is derived from actinomycete.

Preferably, the host cell has isopentenyl diphosphate synthesis ability by a non-mevalonate pathway, and a gene encoding a group of enzymes acting in a mevalonate pathway and/or a gene encoding at least one enzyme acting in a non-mevalonate pathway are/is further introduced, and the gene is expressed in the host cell.

With such a configuration, synthesis ability of IPP which is a supply source of DMAPP is enhanced, and IPP and DMAPP are efficiently supplied. As a result, the recombinant cell of the present aspect has still higher isoprene productivity.

Preferably, the gene encoding at least one enzyme acting in a non-mevalonate pathway is derived from those other than the host cell.

Preferably, the isoprene synthase is derived from plants.

Preferably, the gene encoding isoprene synthase encodes a protein of the following (a), (b) or (c).

(a) a protein having an amino acid sequence represented by SEQ ID NO: 2;

(b) a protein having an amino acid sequence in which 1 to 20 amino acids are deleted, substituted or added in the amino acid sequence represented by SEQ ID NO: 2, and having isoprene synthase activity;

(c) a protein having an amino acid sequence having a homology of 60% or more with the amino acid sequence represented by SEQ ID NO: 2, and having isoprene synthase activity.

Preferably, a gene encoding isopentenyl diphosphate isomerase is further introduced, and the gene is expressed in the host cell.

Since the direct substrate for isoprene synthase is dimethylallyl diphosphate (DMAPP), conversion from IPP to DMAPP is enhanced also by enhancing isopentenyl diphosphate isomerase activity, and the production efficiency of isoprene is improved.

Preferably, a treatment of suppressing an expression amount of geranyl pyrophosphate synthase, neryl pyrophosphate synthase, or farnesyl pyrophosphate synthase is conducted.

IPP can be converted into geranyl pyrohosphate (GPP), neryl pyrophosphate (NPP), or farnesyl pyrophosphate (FPP). And the recombinant cell of the present aspect is subjected to a treatment of suppressing an expression amount of the geranyl pyrohosphate synthase (GPP synthase), neryl pyrophosphate synthase (NPP synthase), or farnesyl synthase (FPP synthase). With such a configuration, waste of IPP which is a supply source of DMAPP is suppressed, and the isoprene productivity is further increased.

Other aspect of the present invention for solving a similar problem is a recombinant cell prepared by introducing a gene imparting the function of converting methanol and/or formic acid to formaldehyde and a gene imparting formaldehyde fixing ability into a host cell having isoprene synthase, wherein the genes are expressed in the host cell, and the recombinant cell is capable of producing isoprene from at least one C1 compound selected from the group consisting of methane, methanol, methylamine, formic acid, formaldehyde, and formamide.

The recombinant cell of the present aspect is prepared by introducing "gene imparting the function of converting methanol and/or formic acid into formaldehyde" and "gene imparting formaldehyde fixing ability" into a host cell having isoprene synthase, and the genes are expressed in the host cell. And it is able to produce isoprene from at least one C1 compound selected from the group consisting of methane, methanol, methylamine, formic acid, formaldehyde, and formamide.

That is, since the recombinant cell of the present aspect is prepared by introducing "gene imparting the function of converting methanol and/or formic acid into formaldehyde", and "gene imparting formaldehyde fixing ability", it has characteristics similar to those of a methylotroph. And since the host cell itself has isoprene synthase, dimethylallyl diphosphate and isopentenyl diphosphate can be converted into isoprene by the action of isoprene synthase. That is, also by the recombinant cell of the present aspect, it is possible to produce isoprene from the aforementioned C1 compound.

Preferably, the gene imparting the function of converting methanol into formaldehyde is a gene encoding methanol dehydrogenase or alcohol oxydase, and the gene imparting the function of converting formic acid into formaldehyde is a gene encoding formaldehyde dehydrogenase.

Preferably, a gene imparting the function of converting methane into methanol is further introduced, and the gene is expressed in the host cell.

Preferably, the gene imparting the function of converting methane into methanol is a gene encoding methane monooxygenase.

Preferably, the recombinant cell has at least one C1 carbon assimilating pathway selected from the group consisting of a serine pathway, a ribulose monophosphate pathway, and a xylulose monophosphate pathway as a fixing pathway of formaldehyde.

Preferably, a gene encoding 3-hexulose-6-phosphate synthase and a gene encoding 6-phospho-3-hexuloisomerase are further introduced, and the genes are expressed in the host cell.

Preferably, the host cell is bacterium or yeast.

Preferably, the host cell has isopentenyl diphosphate synthesis ability by a mevalonate pathway, and a gene encoding at least one enzyme acting in a mevalonate pathway, and/or a gene encoding a group of enzymes acting in a non-mevalonate pathway are/is further introduced, and the gene is expressed in the host cell.

Preferably, the gene encoding at least one enzyme acting in a mevalonate pathway is derived from actinomycete.

Preferably, the host cell has isopentenyl diphosphate synthesis ability by a non-mevalonate pathway, and a gene encoding a group of enzymes acting in a mevalonate pathway, and/or a gene encoding at least one enzyme acting in a non-mevalonate pathway are/is further introduced, and the gene is expressed in the host cell.

Preferably, the gene encoding at least one enzyme acting in a non-mevalonate pathway is derived from those other than the host cell.

Preferably, a gene encoding isoprene synthase is further introduced, and the gene is expressed in the host cell.

With such a configuration, an expression amount of isoprene synthase in the host cell is enhanced, and the isoprene productivity is further increased.

Preferably, the isoprene synthase is derived from plants.

Preferably, the gene encoding isoprene synthase encodes a protein of the following (a), (b) or (c).

(a) a protein having an amino acid sequence represented by SEQ ID NO: 2;

(b) a protein having an amino acid sequence in which 1 to 20 amino acids are deleted, substituted or added in the amino acid sequence represented by SEQ ID NO: 2, and having isoprene synthase activity;

(c) a protein having an amino acid sequence having a homology of 60% or more with the amino acid sequence represented by SEQ ID NO: 2, and having isoprene synthase activity.

Preferably, a gene encoding isopentenyl diphosphate isomerase is further introduced, and the gene is expressed in the host cell.

Preferably, a treatment of suppressing the expression amount of geranyl pyrophosphate synthase, neryl pyrophosphate synthase, or farnesyl pyrophosphate synthase is conducted.

Another aspect of the present invention is a method for producing isoprene including culturing the aforementioned recombinant cell by using at least one C1 compound selected from the group consisting of methane, methanol, methylamine, formic acid, formaldehyde, and formamide as a carbon source, to cause the recombinant cell to produce isoprene.

The present aspect relates to a method for producing isoprene. In the present aspect, the recombinant cell is caused to produce isoprene by culturing the aforementioned recombinant cell by using at least one C1 compound selected from the group consisting of methane, methanol, methylamine, formic acid, formaldehyde, and formamide as a carbon source. According to the present aspect, it is possible to produce isoprene from methanol or the like.

Another aspect of the present invention is a method for producing isoprene including bringing at least one C1 compound selected from the group consisting of methane, methanol, methylamine, formic acid, formaldehyde, and formamide into contact with the aforementioned recombinant cell, to cause the recombinant cell to produce isoprene from the C1 compound.

In the present aspect, isoprene is produced from a C1 compound by bringing at least one C1 compound selected from the group consisting of methane, methanol, methylamine, formic acid, formaldehyde, and formamide into contact with the aforementioned recombinant cell. The present aspect also makes it possible to produce isoprene from methanol or the like.

Advantageous Effect of Invention

According to the recombinant cell of the present invention, it is possible to produce isoprene from methane, methanol, methylamine, formic acid, formaldehyde, or formamide.

According to the method for producing isoprene of the present invention, it is similarly possible to produce isoprene from methane, methanol, methylamine, formic acid, formaldehyde, or formamide.

BRIEF DESCRIPTION OF DRAWINGS

The FIGURE shows an explanatory diagram showing a carbon assimilation metabolism pathway via formaldehyde.

DESCRIPTION OF EMBODIMENT

Hereinafter, embodiments of the present invention will be described. In the present invention, the term "gene" can be replaced by the term "nucleic acid" or "DNA".

One aspect of the present invention is a recombinant cell prepared by introducing a gene encoding isoprene synthase into a host cell which is a methylotroph, wherein the gene is expressed in the host cell, and the recombinant cell is capable of producing isoprene from at least one C1 compound selected from the group consisting of methane, methanol, methylamine, formic acid, formaldehyde, and formamide.

Another aspect of the present invention is a recombinant cell prepared by introducing a gene imparting the function of converting methanol and/or formic acid into formaldehyde, a gene imparting a formaldehyde fixing ability, and a gene encoding isoprene synthase into a host cell, wherein the genes are expressed in the host cell, and the recombinant cell is capable of producing isoprene from at least one C1 compound selected from the group consisting of methane, methanol, methylamine, formic acid, formaldehyde, and formamide.

As described above, a methylotroph is a C1 compound assimilating microorganism that uses a carbon compound not having a C—C bond in the molecule, e.g., methane, methanol, methylamine, dimethylamine, trimethylamine or the like as a sole carbon source or energy source. In general, a methylotroph originally has a carbon assimilation metabolism pathway via formaldehyde, concretely the function (pathway) of converting methanol and/or formic acid to formaldehyde, and a formaldehyde fixing ability (fixing pathway of formaldehyde).

As a fixing pathway of formaldehyde, a serine pathway, a ribulose monophosphate pathway (RUMP pathway), and a xylulose monophosphate pathway (XuMP pathway) shown in the FIGURE can be recited. In general, a methylotroph has a serine pathway, a RUMP pathway, or a XuMP pathway as a carbon assimilation metabolism pathway via formaldehyde.

Here, description will be made for each formaldehyde fixing pathwayin the FIGURE.

The important reaction for formaldehyde fixation by the serine pathway is serine generation reaction of glycine and 5,10-methylene-tetrahydrofolic acid by serine hydroxymethyltransferase. Generation of 5,10-methylene-tetrahydrofolic acid is made by binding formaldehyde to tetrahydrofolic acid. In the serine pathway, one molecule of acetyl CoA is directly generated from one molecule of formaldehyde.

The important reactions for formaldehyde fixation by the RUMP pathway are generation reaction of D-arabino-3-hexulose-6-phosphate from ribulose 5-phosphate (Ru5P) and formaldehyde by 3-hexulose-6-phosphate synthase (hereinafter, also abbreviated as "HPS"), and generation reaction of fructose-6-phosphate (F6P) from D-arabino-3-hexulose-6-phosphate by 6-phosphate-3-hexuloisomerase (hereinafter, also abbreviated as "PHI").

F6P and the like generated in this pathway are also supplied to a glycolytic pathway to subsequently generate acetyl CoA, glyceraldehyde 3-phosaphate (G3P) and pyruvic acid. In the case of F6P, one molecule of F6P is converted to two molecules of G3P, and then two molecules of acetyl CoA are generated via two molecules of pyruvic acid.

The important reaction for formaldehyde fixation by the XuNP pathway is generation reaction of dihydroxyacetone (DHA) and glyceraldehyde-3-phosphate (G3P) from xylulose-5-phosphate (Xu5P) and formaldehyde by dihydroxyacetone synthase. G3P generated in this pathway is also supplied to the glycolytic pathway, and converted to pyruvic acid and acetyl CoA. Dihydroxyacetone is also supplied to the glycolytic pathway by phosphorylation, and can be converted to G3P, pyruvic acid, and acetyl CoA.

The recombinant cell of the present invention is capable of producing isoprene from at least one C1 compound selected from the group consisting of methane, methanol, methylamine, formic acid, formaldehyde, and formamide. For example, a recombinant cell having methanol dehydrogenase or alcohol oxydase is able to convert methanol to formaldehyde.

A recombinant cell having methane monooxydase in addition to methanol dehydrogenase or alcohol oxydase is able to convert methane to methanol, and then convert methanol to formaldehyde.

Further, a recombinant cell having formaldehyde dehydrogenase is able to convert formic acid to formaldehyde.

In general, methylotrophs classified into bacteria (methylotrophic bacteria) are able to synthesize formaldehyde from methane or methanol because they have methane monooxygenase and methanol dehydrogenase. Further, methylotrophs classified into yeast (methylotrophic yeast) are able to synthesize formaldehyde from methanol because they have alcohol oxydase. Further, methylotrophs have formaldehyde dehydrogenase, and are able to convert formic acid to formaldehyde.

The aforementioned methanol dehydrogenase includes pyrroloquinoline quinone (PQQ)-dependent methanol dehydrogenase found in methylotrophs of gram negative bacteria, NAD(P)-dependent methanol dehydrogenase and alcohol dehydrogenase found in methylotrophs of gram positive bacteria, and N,N'-dimethyl-4-nitrosoaniline (DMNA)-dependent methanol oxide reductase (Park H. et al., Microbiology 2010, 156, 463-471) found in methylotrophs of gram positive bacteria. Conversion from methanol to formaldehyde in yeast is usually catalyzed by oxygen-dependent alcohol oxydase.

Also a recombinant cell having amine oxidase or a methylamine dehydrogenase is able to convert methylamine to formaldehyde. These enzymes are known to be inherent in some methylotrophs and *Arthrobacter* bacteria (Anthony C., The Biochemistry of Methylotroph, 1982, Academic Press Inc.)

Also, enzymes that convert formamide to formaldehyde are found in some microorganisms (Anthony C., The Biochemistry of Methylotroph, 1982, Academic Press Inc.)

Additionally, isoprene can be produced via formaldehyde.

While the kind of methylotrophs to be used as a host cell is not particularly limited, for example, those classified into bacteria or yeast can be employed.

Examples of methylotrophic bacteria include bacteria belonging to genus *Methylacidphilum*, genus *Methylosinus*, genus *Methylocystis*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, genus *Methyloversatilis*, genus *Mycobacterium*, genus *Arthrobacter*, genus *Bacillus*, genus *Beggiatoa*, genus *Burkholderia*, genus *Granulibacter*, genus *Hyphomicrobium*, genus *Pseudomonas*, genus *Achromobactor*, genus *Paracoccus*, genus *Crenothrix*, genus *Clonothrix*, genus *Rhodobacter*, genus *Rhodocyclaceae*, genus *Silicibacter*, genus *Thiomicrospira*, and genus *Verrucomicrobia*.

Examples of methylotrophic yeasts include yeast belonging to genus *Pichia*, genus *Candida*, genus *Saccharomyces*, genus *Hansenula*, genus *Torulopsis*, and genus *Kloeckera*. Examples of *Pichia* yeasts include *P. haplophila*, *P. pastoris*, *P. trehalophila*, and *P. lindnerii*. Examples of *Candida* yeasts include *C. parapsilosis*, *C. methanolica*, *C. boidinii*, and *C. alcomigas*. Example of *Saccharomyces* yeast includes *Saccharomyces* metha-nonfoams. Examples of *Hansenula* yeasts include *H. wickerhamii*, *H. capsulata*, *H. glucozyma*, *H. henricii*, *H. minuta*, *H. nonfermentans*, *H. philodendra*, and *H. polymorpha*. Examples of *Torulopsis* yeasts include *T. methanolovescens*, *T. glabrata*, *T. nemodendra*, *T. pinus*, *T. methanofloat*, *T. enokii*, *T. menthanophiles*, *T. methanosorbosa*, and *T. methanodomercqii*.

When the host cell is a non-methylotroph, it is necessary to impart at least "the function of converting methanol and/or formic acid to formaldehyde" because the host cell does not always have a pathway of converting methanol or the like to formaldehyde. Further, it is preferred to impart "the function of converting methane to methanol". Impartation of such functions can be achieved by introducing a gene encoding the aforementioned enzyme into the host cell.

For example, as a gene imparting the function of converting methanol to formaldehyde, a gene encoding methanol dehydrogenase (for example, EC1.1.1.244, EC1.1.2.7) or a gene encoding alcohol oxydase (for example, EC1.13.13) can be used. As a gene imparting the function of converting formic acid to formaldehyde, a gene encoding formaldehyde dehydrogenase (e.g., EC1.2.1.46) can be used. Further, as a gene imparting the function of converting methane to methanol, a gene encoding methane monooxygenase can be used.

Also a plasmid imparting methanol assimilability is known. For example, methanol assimilability of *Bacillus methanolicus* relies on a plasmid encoding a group of enzymes involved in methanol metabolism (Brautaset T. et al., J. Bacteriology 2004, 186(5), 1229-1238). By introducing such a plasmid to a related non-methylotroph, it is possible to impart methanol assimilability. Further, by modifying such a plasmid, it is possible to impart methanol assimilability to various non-methylotrophs.

In the manner as described above, by imparting "the function of converting methanol and/or formic acid to formaldehyde", and further imparting "the formaldehyde fixing ability" to a non-methylotroph, it becomes possible to handle a non-methylotroph similarly to a methylotroph. Impartation of the formaldehyde fixing ability can be realized, for example, by introducing a gene encoding an enzyme acting in the serine pathway, RuMP pathway, or XuMP pathway into a non-methylotroph.

Further description will be made while taking the case of imparting the RuMP pathway as an example. Impartation of the RuMP pathway can be realized, for example, by introducing the aforementioned 3-hexulose-6-phosphate synthase (HPS; e.g., EC4.1.2.43) gene and a 6-phospho-3-hexuloisomerase (PHI; e.g., EC5.3.1.27) gene. That is, ribulose 5-phosphate (Ru5P) and fluctose 6-phosphate (F6P) which are a substrate or a product of the formaldehyde fixing reaction by HPS/PHI generally exist in any organism as metabolic intermediates of the pentose phosphate pathway, and the calvin cycle. Therefore, by introducing HPS/PHI, it is possible to impart the formaldehyde fixing ability to every organism including *Escherichia coli, Bacillus subtilis*, and yeast.

A HPS gene and a PHI gene may be introduced to a host cell originally having the RuMP pathway. As a result, it is possible to enhance the formaldehyde fixing ability by the RUMP pathway. For example, by introducing genes encoding enzymes such as alcohol dehydrogenase such as methanol dehydrogenase (e.g., EC1.1.1.244, EC1.1.2.7), 3-hexulose 6-phosphate synthase (HPS; e.g., EC4.1.2.43), 6-phospho-3-hexuloisomerase (PHI; e.g., EC5.3.1.27) to a microorganism originally having the RuMP pathway or a pathway equivalent to the same, such as *Bacillus subtilis*, it is possible to impart the function of converting methanol to formaldehyde (i.e. methanol assimilability) and to enhance the formaldehyde fixing ability.

HPS gene and PHI gene may be introduced into a host cell which is a methylotroph. That is, by introducing HPS/PHI to a methylotroph having a serine pathway, a RuMP pathway, or a XuMP pathway, it is possible to enhance the formaldehyde fixing ability by the RuMP pathway. As a result, it is possible to improve the formaldehyde resistance of the recombinant cell, and to improve the resistance and assimilability to methanol and formic acid. As a result, it becomes possible to increase the culture efficiency of the recombinant cell and the production efficiency of isoprene.

On the other hand, for imparting the formaldehyde fixing ability by the serine pathway, the aforementioned serine hydroxymethyltransferase (e.g., EC2.1.2.1) gene can be employed. For example, by introducing alcohol dehydrogenase (e.g. methanol dehydrogenase) gene, 5,10-methylenetetrahydrofolate (CH2=H4F) synthase gene, and serine hydroxymethyltransferase (e.g., EC2.1.2.1) gene into a non-methylotroph, it is possible to impart the formaldehyde fixing ability by the methanol assimilability and the serine pathway.

Subsequently, isoprene synthase will be described. Isoprene synthase is not particularly limited as far as its enzyme activity can be exerted in the recombinant cell. Similarly, the gene encoding isoprene synthase is not particularly limited as far as it is normally transcribed and translated in the recombinant cell.

Isoprene synthase is found in many plants. Concrete examples of isoprene synthase include those derived from poplar (*Populus nigra*) (GenBank Accession No.: AM410988.1). Also those derived from *Bacillus subtilis* (SivyTL. et al., Biochem. Biophys. Res. Commu. 2002, 294(1), 71-5) can be recited.

SEQ ID NO: 1 represents a nucleotide sequence of a gene (DNA) encoding isoprene synthase derived from poplar, and a corresponding amino acid sequence, and SEQ ID NO: 2 represents only the amino acid sequence. DNA having the nucleotide sequence represented by SEQ ID NO: 1 is one example of gene encoding isoprene synthase.

Further, the gene encoding isoprene synthase includes at least a gene encoding a protein of the following (a), (b) or (c).
(a) a protein having an amino acid sequence represented by SEQ ID NO: 2;
(b) a protein having an amino acid sequence in which 1 to 20 amino acids are deleted, substituted or added in the amino acid sequence represented by SEQ ID NO: 2, and having isoprene synthase activity;
(c) a protein having an amino acid sequence having a homology of 60% or more with the amino acid sequence represented by SEQ ID NO: 2, and having isoprene synthase activity.

The homology of the amino acid sequence in (c) is more preferably 80% or more, further preferably 90% or more, and particularly preferably 95% or more.

In the recombinant cell of the present invention, other gene may be further introduced in addition to the gene encoding isoprene synthase and so on. As a gene that is introduced, for example, a gene of an enzyme acting in the biosynthesis pathway of isoprenoid described below can be recited.

Every organism including the recombinant cell of the present invention has the isoprenoid biosynthesis pathway involving a mevalonate pathway (also referred to as MVA pathway) or a non-mevalonate pathway (also referred to as MEP pathway), and can synthesize isopentenyl diphosphate (IPP).

The mevalonate pathway is inherent in eukaryotes, and starts with acetyl CoA as a starting substance. Enzymes acting in the mevalonate pathway include, in the order from the upstream, acetyl CoA acetyl transferase, HMG-CoA synthase, HMG-CoA reductase, mevalonate kinase, 5-phosphomevalonate kinase, diphosphomevalonate decarboxylase, and isopentenyl diphosphate isomerase.

On the other hand, the non-mevalonate pathway is inherent in prokaryotes and chloroplasts and plastids, and starts with glyceraldehyde 3-phosphate and pyruvic acid as starting substances. Enzymes acting in the non-mevalonate pathway include, in the order from the upstream, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase.

In one embodiment, when the host cell has IPP synthesis ability by the mevalonate pathway, (i) a gene encoding at least one enzyme acting in the mevalonate pathway, and/or (ii) a gene encoding a group of enzymes acting in the non-mevalonate pathway are/is further introduced. Introduction of the gene of (i) enhances the IPP synthesis ability by the mevalonate pathway. Also, introduction of the gene of (ii) results in synthesis of IPP from both the mevalonate pathway and the non-mevalonate pathway, and enhances the IPP synthesis ability. Enhancement of the IPP synthesis ability results in more efficient production of isoprene.

In another embodiment, when the host cell has IPP synthesis ability by the non-mevalonate pathway, (iii) a gene encoding a group of enzymes acting in the mevalonate pathway, and/or (iv) a gene encoding at least one enzyme acting in the non-mevalonate pathway are/is further introduced. Introduction of the gene of (iii) results in synthesis of IPP from both the mevalonate pathway and the non-mevalonate pathway, and therefore, enhances the IPP synthesis ability. Also, introduction of the gene of (iv) enhances the IPP synthesis ability by the non-mevalonate pathway. Enhancement of the IPP synthesis ability results in more efficient production of isoprene.

As described above, as the group of enzymes acting in the mevalonate pathway, acetyl CoA acetyl transferase, HMG-CoA synthase, HMG-CoA reductase, mevalonate kinase, 5-phosphomevalonate kinase, diphosphomevalonate decarboxylase, and isopentenyl diphosphate isomerase can be recited.

In the case of introducing the gene of (i), the gene to be introduced can be selected so that one or more enzymes selected from the group consisting of, for example, acetyl CoA acetyl transferase, HMG-CoA synthase, HMG-CoA reductase, mevalonate kinase, 5-phosphomevalonate kinase, diphosphomevalonate decarboxylase, and isopentenyl diphosphate isomerase are expressed in the host cell. For example, one or more enzymes can be selected from the group of enzymes, and a gene encoding the enzyme can be introduced into the host cell.

In the case of introducing the gene of (iii), the gene to be introduced can be selected so that the group of enzymes consisting of, for example, HMG-CoA synthase, HMG-CoA reductase, mevalonate kinase, 5-phosphomevalonate kinase, diphosphomevalonate decarboxylase, and isopentenyl diphosphate isomerase is expressed in the host cell.

As described above, the group of enzymes acting in the non-mevalonate pathway include DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase.

In the case of introducing the gene of (ii), the gene to be introduced can be selected so that the group of enzymes consisting of, for example, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase is expressed in the host cell.

In the case of introducing the gene of (iv), the gene to be introduced can be selected so that one or more enzymes selected from the group consisting of, for example, DOXP synthase, DOXP reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, HMB-PP synthase and HMB-PP reductase are expressed in the host cell. For example, one or more enzymes can be selected from the group of enzymes, and a gene encoding the enzyme can be introduced into the host cell.

The mevalonate pathway is inherent in all eukaryotes, but is also found in those other than eukaryotes. Examples of those having a mevalonate pathway other than eukaryotes include *Streptomyces* sp. Strain CL190 (Takagi M. et al., J. Bacteriol. 2000, 182 (15), 4153-7), and *Streptomyces griseolosporeus* MF730-N6 (Hamano Y. et al., Biosci. Biotechnol. Biochem. 2001, 65(7), 1627-35) which are actinomycetes. In bacteria, *Lactobacillus helveticus* (Smeds A et al., DNA seq. 2001, 12(3), 187-190), *Corynebacterium amycolatum, Mycobacterium marinum, Bacillus coagulans, Enterococcus faecalis, Streptococuss agalactiae, Myxococcus xanthus* and so on (Lombard J. et al., Mol. Biol. Evol. 2010, 28(1), 87-99) can be recited. In archaea, genus *Aeropyrum*, genus *Sulfolobus*, genus *Desulfurococcus*, genus *Thermoproteus*, genus *Halobacterium*, genus *Methanococcus*, genus *Thermococcus*, genus *Pyrococcus*, genus *Methanopyrus*, genus *Thermoplasma* and so on (Lombard J. et al., Mol. Biol. Evol. 2010, 28 (1), 87-99) can be recited. For example, as the gene of (i) or (iii), the one derived from the foregoing organisms can be used.

As an example for enhancing IPP synthesis of a bacterium, it is preferred to introduce a group of mevalonate pathway enzymes that is not inherent in the bacterium so as to avoid the gene expression control of the host.

The enzymes acting in the non-mevalonate pathway encoded by the gene of (ii) or (iv) are preferably derived from those other than the host cell. With such a constitution, it is possible to avoid reaction suppression by a reaction product.

In the case of a host cell having a serine pathway, it is particularly preferred to introduce a gene of a group of mevalonate pathway enzymes as a foreign gene so as to directly generate acetyl CoA from the serine pathway which is a formaldehyde fixing pathway.

The enzymes acting in the mevalonate pathway or the non-mevalonate pathway encoded by the gene of (i) to (iv) may be naturally occurring enzymes or enzymes modified therefrom. For example, amino acid substitution variants of each enzyme, and polypeptides that are partial fragments of each enzyme and have equivalent enzyme activity are also applicable.

Since the direct substrate for isoprene synthase is dimethylallyl diphosphate (DMAPP), conversion from IPP to DMAPP is enhanced also by enhancing isopentenyl diphosphate isomerase activity, and the production efficiency of isoprene is improved. Accordingly, an isopentenyl diphosphate isomerase gene may further be introduced as a foreign gene. The isopentenyl diphosphate isomerase gene in this case is preferably derived from the same as or related species with the host.

By conducting a treatment of suppressing the expression amount of geranyl pyrohosphate synthase (GPP synthase), neryl pyrophosphate synthase (NPP synthase), or farnesyl pyrophosphate synthase (FPP synthase) on the recombinant, it is possible to further improve the isoprene productivity. That is, by this treatment, conversion from IPP to GPP, NPP, or FPP is suppressed, and the waste of IPP which is a supply source of DMAPP is suppressed.

As the treatment, various treatments on the gene encoding GPP synthase, NPP synthase, or FPP synthase, for example, introduction of mutation to the gene (modification of codon, e.g. knockout and so on), modification of a promoter, modification of a SD sequence and so on are recited.

A still another aspect of the present invention is a recombinant cell prepared by introducing a gene imparting the function of converting methanol and/or formic acid to formaldehyde and a gene imparting formaldehyde fixing ability into a host cell having isoprene synthase, wherein the genes are expressed in the host cell, and the recombinant cell is capable of producing isoprene from at least one C1 compound selected from the group consisting of methane, methanol, methylamine, formic acid, formaldehyde, and formamide.

As a host cell having isoprene synthase that can be employed in this aspect, bacteria belonging to genus *Bacillus*, genus *Acinetobacter*, genus *Agrobacterium*, genus *Erwinia*, genus *Pseudomonas* and so on as described in U.S. Pat. No. 5,849,970 can be recited.

Also in this aspect, any embodiment described above can be directly applied. For example, in the present aspect, the aforementioned example can be directly applied regarding "gene imparting "the function of converting methanol and/or formic acid to formaldehyde" and "gene imparting formaldehyde fixing ability". That is, genes respectively encoding methanol dehydrogenase, alcohol oxydase, formaldehyde dehydrogenase, methane monooxygenase and so on can be introduced into the host cell.

Also in the present aspect, a gene encoding 3-hexulose 6-phosphate synthase (HPS) and a gene encoding 6-phospho-3-hexuloisomerase (PHI) may further be introduced.

Further, also in the present aspect, a gene of enzyme that acts in the isoprenoid biosynthesis pathway may be introduced into the host cell. For example, embodiments using the genes of (i) to (iv) can also be applied to the present aspect.

In the present aspect, a gene encoding isoprene synthase may further be introduced into the host cell. According to the present embodiment, since foreign isoprene synthase is synthesized in addition to isoprene synthase that is inherent in the host cell, the isoprene productivity is further improved. The isoprene synthase gene to be introduced is not particularly limited, and for example, isoprene synthase gene derived from poplar can be used. Also, isoprene synthase gene derived from the host cell may further be introduced.

Also in this aspect, a treatment for suppressing the expression amount of geranyl pyrohosphate synthase (GPP synthase), neryl pyrophosphate synthase (NPP synthase), or farnesyl pyrophosphate synthase (FPP synthase) may be conducted on the recombinant.

The method of introducing a gene into the host cell is not particularly limited, and may be selected appropriately depending on the kind of the host cell and the like. For example, a vector that can be introduced into the host cell and can allow expression of the gene incorporated therein may be used.

For example, when the host cell is a prokaryote such as a bacterium, a vector that can self duplicate or can be incorporated in chromosome in the host cell, and contains a promoter at the position allowing transcription of the inserted gene can be used. For example, it is preferred to construct in the host cell a series of structures including a promoter, a ribosome binding sequence, the above gene and a transcription termination sequence by using the vector.

For example, as a method of incorporating into chromosome of a methylotroph bacterium, exemplified is a method of destroying a target gene in *Methylobacillus flagellatus* having a ribulose monophosphate pathway, and in *Methylobacterium extorquencs* having a serine pathway (Chistoserdova L. et al., Microbiology 2000, 146, 233-238; Chistoserdov A Y., et al., J. Bacteriol 1994, 176, 4052-4065).

While these are the methods for introducing a gene into a genome using cyclic DNA, a method for introducing a gene into genome using a linear DNA is also developed in *Methylophilus* bacteria and the like (see JP 2004-229662 A). In general, genomic recombination is more efficient by linear DNA than by cyclic DNA when the DNA is less susceptible to degradation by the host cell. Generally, in a homologous recombination method, it is preferred to target a gene existing in multi copies on the genome likewise an inverted-repeat sequence. As a technique for introducing multi copies into a genome, a method of carrying on a transposon is also known besides the homologous recombination. As a method of introducing a gene into a methylotrophic bacterium by a plasmid, for example, pAYC32 (Chistoserdov A Y., et al., Plasmid 1986, 16, 161-167), pRP301 (Lane M., et al., Arch. Microbiol. 1986, 144(1), 29-34), pBBR1, pBHR1 (Antoine R. et al., Molecular Microbiology 1992, 6, 1785-1799), and pCM80 (Marx C J. et al., Microbiology 2001, 147, 2065-2075) which are broad host range vectors are known.

A method of introducing a gene in methylotrophic yeast is established mainly in *Pichia pastoris*, and vectors such as pPIC3.5K, pPIC6, pGAPZ, and pFLD (available from Invitrogen) are commercially available.

As a plasmid that can be used for gene introduction into *Bacillus* bacteria, pMTLBS72 (Nguyen H D. Et al., Plasmid 2005, 54(3), 241-248), pHT01 (available from Funakoshi Co., Ltd.), pHT43 (available from Funakoshi Co., Ltd.) and so on are available for *Bacillus subtilis*, p3STOP1623 hp (available from Funakoshi Co., Ltd.), pSP$_{YocH}$hp (available from Funakoshi Co., Ltd.) and so on are available for *Bacillus megaterium*, and pNI DNA (available from TAKARA BIO INC.) and so on are available for *Bacillus brevis*.

In introducing plural kinds of genes by using a vector, the genes may be incorporated into one vector, or incorporated into different vectors. Further, in incorporating a plurality of genes into one vector, the genes may be expressed under a common promotor, or may be expressed under different promotors. As an example of introducing plural kinds of genes, an embodiment of introducing the gene of (i) to (iv), or HPS/PHI gene in addition to "gene encoding isoprene synthase" when the host cell is a methylotroph is recited.

As describe above, while the known vectors that can be used in methylotroph and so on have been shown, the region involved in transcription control and replication regions such as promotor and terminator can be modified depending on the purpose. The modification includes change to other natural gene sequence in each host cell or its related species, and change to an artificial gene sequence.

It is possible to further improve the productivity of isoprene by combining a variation technique such as mutation or genome shuffling in addition to the modification by the gene introduction as described above.

In one aspect of the method for producing isoprene, the recombinant cell is cultured by using at least one C1 compound selected from the group consisting of methane, methanol, methylamine, formic acid, formaldehyde, and formamide as a carbon source, and the recombinant cell is caused to produce isoprene. Regarding these C1 compounds used as a carbon source, one compound or a combination of two or more compounds may be used. These C1 compounds are preferably used as a main carbon source, and more preferably as a sole carbon source.

In the case of obligate methylotrophs, basically a synthetic culture medium containing a C1 compound as a sole carbon source is used, and addition of small amounts of natural culture medium such as yeast extract, corn steep liquor, and meat extract and vitamins to this culturemedium promotes proliferation of bacteria. In the case of facultative methylotrophs, carbohydrates, lipids and the like substances other than C1 compounds may be used as a carbon source in the bacterial proliferation stage, and in this case, the carbon source can be changed to the above C1 compound in the isoprene production stage. Microorganisms can be cultured in any of aerobic, microaerobic, or anaerobic condition depending on the purpose. Any of the batch culture, feeding culture, and continuous culture can be employed.

For example, when methanol is used as a carbon source, it is typically used at a concentration of 1.0% (v/v) in the case of bacteria, or a concentration of 3.0% (v/v) or less in the case of yeasts, however, when the resistance to these is artificially modified, the culture can be also conducted with methanol of higher concentrations.

In another aspect of the method for producing isoprene of the present invention, at least one C1 compound selected from the group consisting of methane, methanol, methylamine, formic acid, formaldehyde, and formamide are brought into contact with the recombinant cell, and the recombinant cell allows to produce isoprene from the C1 compound. That is, regardless of whether cell division (cell proliferation) is involved or not, it is possible to produce isoprene by bringing the C1 compound into contact with the recombinant cell. For example, it is possible to continuously produce isoprene by continuously supplying an immobilized recombinant cell with the C1 compound.

Also in the present aspect, regarding these C1 compounds, only one C1 compound may be used, or a combination of two or more C1 compounds may be used.

The produced isoprene is accumulated in the cell or released outside the cell. For example, by collecting, isolating and purifying the isoprene released outside the cell, it is possible to acquire purified isoprene.

In the following, the present invention will be described more specifically by way of examples. However, the present invention is not limited to these examples.

Example 1

Introduction of isoprene synthase gene into a methylotroph having the XuMP pathway, and production of isoprene from methanol using a recombinant In the present example, methanol assimilating yeast *Pichia pastolis* GS115 strain (available from Invitrogen) was used as a methylotroph having a XuMP pathway.

Using total RNA derived from leaf of poplar (*Populus nigra*) as a template, a gene encoding isoprene synthase (IspS) from poplar (IspS gene from poplar, SEQ ID NO: 1, GenBank Accession No.: AM410988.1) was amplified by RT-PCR using primers represented by SEQ ID NO: 3 and SEQ ID NO: 4. The obtained amplified DNA fragment was cloned into pT7-Blue T vector (available from TAKARA BIO INC.) to construct pT7IS. The pT7IS was cut with BamHI to obtain IspS gene. The obtained IspS gene was introduced into BamHI site of pPIC3.5K (available from Invitrogen) to construct a vector pPCIPS in which isoprene synthase gene is introduced.

Introduction of isoprene synthase gene by means of pPCIPS into *Pichia pastoris* GS115 strain was conducted according to the Invitrogen Manual "Version D 032002/25-0156". For obtaining a multi-copy transformant, Geneticin (available from Invitrogen) tolerant strain at a concentration of 1.5 mg/mL was acquired. In this manner, methanol assimilating yeast GS115IPS strain having a plurality of copies of foreign isoprene synthase gene was constructed. As a control strain, GS11535K strain in which only pPIC3.5K was introduced having tolerance to Geneticin at a concentration of 1.5 mg/mL was obtained.

Each of GS115IPS strain and GS11535K strain was cultured aerobically at 30° C. for 64 hours in 20 mL of synthetic A culture containing methanol as a sole carbon source (containing 18 g of $H_3PO_4$, 14.28 g of $K_2SO_4$, 3.9 g of KOH, 0.9 g of $CaSO_4.2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 20 mL of methanol per 1 L). After collecting the cells, the cells were further cultured in 45 mL of synthetic A culture medium in a 125 mL vial sealed with a butyl rubber plug at 30° C. for another 16 hours under shaking. After end of the culture, the gas phase component was analyzed by GC/MS. Isoprene was not detected in GS11535K strain, but was detected in GS115IPS strain. These revealed that the present example allowed production of isoprene by eukaryotic microorganism (yeast) via a XuMP pathway which is one of methanol assimilating pathways.

Example 2

Introduction of methanol dehydrogenase, HPS gene, PSI gene, and isoprene synthase gene into a non-methylotroph, and production of isoprene from methanol by a recombinant In the present example, *Bacillus subtilis* was used as a non-methylotroph.

(Preparation of Various Genes)

NADP-dependent methanol dehydrogenase (MDH) gene of SEQ ID NO: 5 was amplified from genomic DNA of *Bacillus methanolicus* (NCIMB 13114) by PCR using primers of SEQ ID NO: 7 and SEQ ID NO: 8. The amplified DNA fragment was cloned into pT7 Blue-T vector to construct pT7BMmdh.

3-hexulose 6-phosphate synthase (HPS) gene of SEQ ID NO: 9 was amplified from genomic DNA of *Methylomonas aminofaciens* by PCR using primers of SEQ ID NO: 11 and SEQ ID NO: 12. The amplified DNA fragment was cloned into pT7 Blue-T vector to construct pT7MAhps.

6-phospho-3-hexuloisomerase (PHI) gene of SEQ ID NO: 13 was amplified from genomic DNA of *Methylomonas aminofaciens* by PCR using primers of SEQ ID NO: 15 and SEQ ID NO: 16. The amplified DNA fragment was cloned into pT7 Blue-T vector to construct pT7MAphi.

PCR was conducted by using pT7IS having isoprene synthase (IspS) gene prepared in Example 1 as a template, and primers of SEQ ID NO: 17 and SEQ ID NO: 18. The amplified DNA fragment was cloned into pT7 Blue-T vector to construct pT7IS2.

(Construction of Various Expression Vectors)

The cloning vector pT7MAhps was cut with BglII and BamHI to cut out hps gene. The hps gene was introduced into BamHI site of an expression vector for *Bacillus subtilis* pHT01 (MoBiTec) to prepare pHTh.

By cutting the cloning vector pT7MAphi with BglII and BamHI, PHI gene was cut out. The PHI gene was introduced into BamHI site of pHTh to prepare pHThp.

By cutting the cloning vector pT7BMmdh with BglII and BamHI, MDH gene was cut out. The MDH gene was introduced into BamHI site of pHThp to prepare pHThpm.

Further, by cutting pT7IS2 with BamHI and SmaI, IspS gene was cut out. The IspS gene was introduced into BamHI/SmaI site of pHThpm to construct pHThpmIS. The expression vector pHThpmIS has an operon in which HPS gene, PHI gene, MDH gene, and IspS gene are arranged in this order downstream of promotor of pHT01.

As a control, an expression vector pHThpIS having only HPS gene, PHI gene, and IspS gene was prepared in the same manner as described above. Similarly, an expression vector pHThpm having only HPS gene, PHI gene, and MDH gene was prepared.

According to the manual of MoBiTec "*Bacillus subtilis* Expression Vectors", each expression vector was introduced into *Bacillus subtilis* and a recombinant (recombinant cell) was prepared. In this manner, BShpmIS strain having the expression vector pHThpmIS, BShpIS strain having the expression vector pHThpIS, and BShpm strain having the expression vector pHThpm were prepared, respectively.

Each recombinant was aerobically cultured at 37° C. in 20 mL of a methanol assimilating inductive culture medium (containing 10 mL of methanol, 3 g of ammonium phosphate, 1 g of potassium chloride, 0.1 g of magnesium sulfate heptahydrate, 0.5 g of yeast extract, 0.01 mM IPTG, and 5 mg of chloramphenicol in 1 L of tap water). The cells were collected at the point of time when OD600 of the culture liquid reached 1.0 to 1.2. All the collected cells were added to 45 mL of a methanol assimilating inductive culture medium similar to that described above (provided that IPTG concentration was 0.1 mM), and were further cultured in a 125 mL vial sealed with a butyl rubber plug at 37° C. for 24 hours under shaking. After end of the culture, the gas phase component was analyzed by GC/MS.

Consequently, while BShpmIS strain and BShpm strain grew sufficiently, BShpIS strain not having MDH little grew.

Regarding isoprene production, isoprene was detected in BShpmIS strain. Conversion efficiency from the assimilated methanol to isoprene in BShpmIS strain was 14%. Although isoprene was slightly detected in BShpm strain, conversion efficiency from the assimilated methanol to isoprene was as small as about 0.3%.

These revealed that by introducing MDH gene, HPS gene, and PHI gene to *Bacillus subtilis* which is a non-methylotroph, efficient growth in a culture medium containing methanol as a main carbon source was enabled, and by introducing IspS gene, isoprene was generated efficiently.

Example 3

Preparation of a methylotroph having a serine pathway into which MVA pathway gene and isoprene synthase gene are introduced, and isoprene production from methanol by a recombinant In the present example, an isoprene producing strain was prepared by using *Methylobacterium extorquens* (ATCC 55366) as a methylotroph having a serine pathway, and introducing IspS gene and a mevalonate pathway gene cluster derived from actinomycete into this strain.

A DNA fragment containing IspS gene derived from poplar was prepared by PCR using pT7IS prepared in Example 1 as a template, and primers represented by SEQ ID NO: 19 and SEQ ID NO: 20. This DNA fragment was cloned into pT7-Blue T vector to prepare pT7IS3.

A DNA fragment containing a gene encoding a group of a mevalonate pathway enzymes of *S. griseolosporeus* (SEQ ID NO: 23) was amplified by PCR using genomic DNA of actinomycete, *Streptomyces griseolosporeus* (*Kitasatospora griseola*) as a template, and primers represented by SEQ ID NO: 21 and SEQ ID NO: 22. This DNA fragment includes a gene cluster encoding mevalonate kinase, mevalonate diphosphate decarboxylase, Phosphomevalonate kinase, IPP isomerase, HMG-CoA (3-hydroxy-3-methylglutaryl coenzyme A) reductase (HMGR), and HMG-CoA synthase. The obtained amplified DNA fragment was cloned into pT7-Blue T vector to construct pT7SMV.

The pT7IS3 was cut with BamHI and KpnI to obtain IspS gene. The IspS gene was introduced into BamHI/KpnI site of pCM80 (Marx C J. et al., Microbiology 2001, 147, 2065-2075) which is a broad host range vector to prepare pC80IS. The pT7SMV was cut with KpnI to obtain a fragment containing an actinobacterial MVA pathway gene and a terminator sequence. The fragment was introduced into KpnI site of the pC80IS to construct pC80ISMV. The expression vector pC80ISMV has IspS gene and a group of genes of actinobacterial MVA pathway enzymes downstream of the promotor.

The expression vector pC80IS was introduced into *M. extorquens* by electroporation to obtain ME-IS strain. The expression vector pC80ISMV was introduced into *M. extorquens* by electroporation to obtain ME-ISMV strain. As a control, the expression vector pCM80 was introduced into *M. extorquens* by electroporation to obtain ME-CM80 strain.

ME-IS strain, ME-ISMV strain, or ME-CM80 strain was aerobically cultured at 30° C. in 20 mL of synthetic B culture medium containing methanol as a sole carbon source (containing 18 g of $H_3PO_4$, 14.28 g of $K_2SO_4$, 3.9 g of KOH, 0.9 g of $CaSO_4$, $2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 5 mL of methanol, and 10 mg of tetracycline per 1 L). The cells were collected at the point of time when OD600 of the culture liquid reached 1.0 to 1.2. All the collected cells were added to 45 mL of synthetic B culture medium as described above, and were cultured in a 125 mL vial sealed with a butyl rubber plug at 30° C. for 16 hours under shaking. After end of the culture, the gas phase component was analyzed by GC/MS.

Consequently, isoprene was detected in ME-IS strain and ME-ISMV strain. Conversion efficiency from the assimilated methanol to isoprene was 8% in ME-IS strain and 27% in ME-ISMV strain. In ME-CM80 strain, isoprene was not detected.

These revealed that by introducing MVA pathway gene and isoprene synthase gene into a methylotroph having a serine pathway, it was possible to efficiently produce isoprene from methanol.

Example 4

Introduction of isoprene synthase gene into methylotroph having a RUMP pathway and isoprene production from methanol using a recombinant In the present example, an isoprene producing strain was prepared by using *Methylophilus methylotrophus* (ATCC 53528) as a methylotroph having a RuMP pathway, and introducing IspS gene into this strain.

A DNA fragment containing IspS gene was amplified by PCR using pT7IS prepared in Example 1 as a template and primers of SEQ ID NO: 19 and SEQ ID NO: 24. This DNA fragment was cloned into pT7Blue-T vector to prepare pT7IspS4. The pT7IspS4 was cut with BamHI and KpnI to obtain a DNA fragment containing IspS gene and a terminator sequence. This DNA fragment was introduced into BamHI/KpnI site of pCM80 (Example 3) to construct an IspS expression vector pM80IS. The pM80IS was introduced to *M. methylotrophus* by electroporation to obtain MM-80IS strain.

Also a gene cluster including *Escherichia coli* IDI (isopentenyl diphosphate isomerase) gene and popular IspS gene (SEQ ID NO: 25) was introduced into BamHI/KpnI site of the pCM80 to construct pC80IDIS. The pC80IDIS was introduced into *M. methylotrophus* by electroporation to obtain MM-80IDIS strain.

As a control, the pCM80 was introduced into *M. methylotrophus* by electroporation to obtain MM-80 strain.

MM-80IS strain, MM-80IDIS strain, or MM-80 strain was aerobically cultured at 37° C. in 20 mL of synthetic B culture medium containing methanol as a sole carbon source used in Example 3 (provided that the methanol concentration was set at 1% (v/v)). The cells were collected at the point of time when OD600 of the culture liquid reached 1.0 to 1.2. All the collected cells were added to 45 mL of synthetic B culture medium as described above, and were cultured in a 125 mL vial sealed with a butyl rubber plug at 37° C. for 16 hours under shaking. After end of the culture, the gas phase component was analyzed by GC/MS.

Consequently, isoprene was detected in MM-80IS strain and MM-80IDIS strain. Conversion efficiency from the assimilated methanol to isoprene was 12% in MM-80IS strain, and 19% in MM-80IDIS strain. On the other hand, isoprene was not detected in MM-80 strain.

These revealed that by introducing an isoprene synthase gene into a methylotroph having a RUMP pathway, it was possible to efficiently produce isoprene from methanol. It was also revealed that isoprene synthesis was promoted by introduction of IDI gene.

Example 5

Introduction of methanol dehydrogenase(MDH) gene, HPS gene, PHI gene, and IspS gene into *Escherichia coli*, and production of isoprene from methanol by a recombinant A DNA fragment (hpmIS) containing HPS gene, PHI gene, MDH gene and IspS gene was amplified by PCR using the expression vector pHThpmIS prepared in Example 2 as a template, and primers of SEQ ID NOs: 26 and 27. This amplified DNA fragment was cloned into pT7Blue-T vector to prepare pT7hpmIS. The pT7hpmIS was cut with NcoI and BamHI to obtain a DNA fragment containing hpmIS gene. This DNA fragment was introduced into NcoI/BamHI site of pET23d (available from Novagen) to construct expression vector pThpmIS in *Escherichia coli*. The expression vector pThpmIS was introduced into *Escherichia coli* Rosetta (DE3) (available from Novagen) to obtain *Escherichia coli* RHPMI strain.

A DNA fragment (hpIS) containing HPS gene, PHI gene, and IspS gene was amplified by PCR using the expression vector pHThpIS prepared in Example 2 as a template and primers of SEQ ID NOs: 26 and 27. This amplified DNA fragment was cloned into pT7Blue-T vector to prepare pT7hpIS. The pT7hpIS was cut with NcoI and BamHI to obtain a DNA fragment containing hpIS gene. This DNA fragment was introduced into NcoI/BamHI site of pET23d (available from Novagen) to construct expression vector pThpIS in *Escherichia coli*. The expression vector pThpIS was introduced into *Escherichia coli* Rosetta (DE3) to obtain *Escherichia coli* RHPI strain.

A DNA fragment (hpm) containing HPS gene, PHI gene, and MDH gene was amplified by PCR using the expression vector pHThpm prepared in Example 2 as a template and primers of SEQ ID NOs: 26 and 28. This amplified DNA fragment was cloned into pT7Blue-T vector to prepare pT7hpm. The pT7hpm was cut with NcoI and BamHI to obtain a DNA fragment containing hpm gene. This DNA fragment was introduced into NcoI/BamHI site of pET23d (available from Novagen) to construct expression vector pThpm in *Escherichia coli*. The expression vector pThpm was introduced into *Escherichia coli* Rosetta (DE3) to obtain *Escherichia coli* RHPM strain.

Each recombinant *Escherichia coli* was cultured aerobically at 37° C. in 20 mL of methanol assimilative synthetic C culture medium containing 0.05 mM IPTG (containing 18 g of $H_3PO_4$, 14.28 g of $K_2SO_4$, 3.9 g of KOH, 0.9 g of $CaSO_4.2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 5 mL of methanol, 34 mg of chloramphenicol, and 100 mg of ampicillin per 1 L). The cells were collected at the point of time when OD600 of the culture liquid reached 1.0 to 1.2. All the collected cells were added to 45 mL of synthetic C culture medium of the same composition described above, and were cultured in a 125 mL vial sealed with a butyl rubber plug at 37° C. for 24 hours under shaking. After end of the culture, the gas phase component was analyzed by GC/MS.

Isoprene was detected only in RHPMI strain. Conversion efficiency from the assimilated methanol to isoprene in RHPMI strain was 14%. The RHPI strain was completely unable to grow. The RHPM strain was able to grow, but generation of isoprene was not detected.

The invention claimed is:

1. A recombinant cell prepared by introducing a gene encoding isoprene synthase, into a host cell which is methylotroph, wherein:
   the methylotroph host cell belongs to genus *Pichia*, genus *Methylobacterium*, or genus *Methylophilus*,
   the gene encoding isoprene synthase is expressed in the host cell,
   the recombinant cell is prepared by further introducing into the host cell six additional genes encoding HMG-CoA synthase, HMG-CoA reductase, mevalonate kinase, 5-phosphomevalonate kinase, diphosphomevalonate decarboxylase, and isopentenyl diphosphate isomerase,
   the six additional genes are expressed in the host cell,
   the recombinant cell produces isoprene from methanol, and
   the conversion efficiency of methanol to isoprene is 27% or more.

2. The recombinant cell according to claim 1, wherein the gene encoding at least one enzyme acting in a mevalonate pathway is derived from actinomycete.

3. The recombinant cell according to claim 1, wherein a gene encoding isopentenyl diphosphate isomerase is further introduced, and the gene is expressed in the host cell.

4. The recombinant cell according to claim 1, wherein a treatment of suppressing an expression amount of geranyl pyrohosphate synthase, neryl pyrophosphate synthase, or farnesyl pyrophosphate synthase is conducted.

5. The recombinant cell according to claim 1,
   wherein the gene encoding isoprene synthase encodes a protein of the following (a), (b) or (c):
   (a) a protein having the amino acid sequence of SEQ ID NO: 2;
   (b) a protein having an amino acid sequence in which 1 to 20 amino acids are deleted, substituted or added in the amino acid sequence of SEQ ID NO: 2, and having isoprene synthase activity; or
   (c) a protein having an amino acid sequence having a homology of 90% or more with the amino acid sequence of SEQ ID NO: 2, and having isoprene synthase activity.

6. A method for producing isoprene comprising culturing the recombinant cell according to claim 1 by using methanol as a carbon source, to cause the recombinant cell to produce isoprene.

7. A method for producing isoprene comprising bringing methanol into contact with the recombinant cell according to claim 1, to cause the recombinant cell to produce isoprene from the methanol.

* * * * *

SEQUENCE LISTING

```
<160> NUMBER OF SEQ ID NOS: 28

<210> SEQ ID NO 1
<211> LENGTH: 1788
<212> TYPE: DNA
<213> ORGANISM: Populus nigra
<220> FEATURE:
<221> NAME/KEY: CDS
<222> LOCATION: (1)..(1788)
<223> OTHER INFORMATION:

<400> SEQUENCE: 1 atg gca act gaa tta ttg tgc ttg cac cgt cca atc tca ctg aca cac      48
Met Ala Thr Glu Leu Leu Cys Leu His Arg Pro Ile Ser Leu Thr His
1               5                   10                  15 aaa ttg ttc aga aat ccc ttg cct aaa gtc atc cag gcc act ccc tta      96
Lys Leu Phe Arg Asn Pro Leu Pro Lys Val Ile Gln Ala Thr Pro Leu
            20                  25                  30 act ttg aaa ctc aga tgt tct gta agc aca gaa aac gtc agc ttc aca     144
Thr Leu Lys Leu Arg Cys Ser Val Ser Thr Glu Asn Val Ser Phe Thr
        35                  40                  45 gaa aca gaa aca gaa acc aga agg tct gcc aat tat gaa cca aat agc     192
Glu Thr Glu Thr Glu Thr Arg Arg Ser Ala Asn Tyr Glu Pro Asn Ser
    50                  55                  60 tgg gat tat gat tat ttg ctg tct tcg gac act gac gaa tcg att gaa     240
Trp Asp Tyr Asp Tyr Leu Leu Ser Ser Asp Thr Asp Glu Ser Ile Glu
65                  70                  75                  80 gta tac aaa gac aag gcc aaa aag ctg gag gct gag gtg aga aga gag     288
Val Tyr Lys Asp Lys Ala Lys Lys Leu Glu Ala Glu Val Arg Arg Glu
                85                  90                  95 att aac aat gaa aag gca gag ttt ttg act ctg cct gaa ctg ata gat     336
Ile Asn Asn Glu Lys Ala Glu Phe Leu Thr Leu Pro Glu Leu Ile Asp
            100                 105                 110 aat gtc caa agg tta gga tta ggt tac cgg ttc gag agt gac ata agg     384
Asn Val Gln Arg Leu Gly Leu Gly Tyr Arg Phe Glu Ser Asp Ile Arg
        115                 120                 125 aga gcc ctt gat aga ttt gtt tct tca gga gga ttt gat gct gtt aca     432
Arg Ala Leu Asp Arg Phe Val Ser Ser Gly Gly Phe Asp Ala Val Thr
    130                 135                 140 aaa act agc ctt cat gct act gct ctt agc ttc agg ctt ctc aga cag     480
Lys Thr Ser Leu His Ala Thr Ala Leu Ser Phe Arg Leu Leu Arg Gln
145                 150                 155                 160 cat ggc ttt gag gtc tct caa gaa gcg ttc agc gga ttc aag gat caa     528
His Gly Phe Glu Val Ser Gln Glu Ala Phe Ser Gly Phe Lys Asp Gln
                165                 170                 175 aat ggc aat ttc ttg aaa aac ctt aag gag gac atc aag gca ata cta     576
```

```
            Asn Gly Asn Phe Leu Lys Asn Leu Lys Glu Asp Ile Lys Ala Ile Leu
                        180                 185                 190 agc cta tat gaa gct tca ttt ctt gcc tta gaa gga gaa aat atc ttg         624
Ser Leu Tyr Glu Ala Ser Phe Leu Ala Leu Glu Gly Glu Asn Ile Leu
            195                 200                 205 gat gag gcc aag gtg ttt gca ata tca cat cta aaa gag ctc agc gaa         672
Asp Glu Ala Lys Val Phe Ala Ile Ser His Leu Lys Glu Leu Ser Glu
210                 215                 220 gaa aag att gga aaa gac ctg gcc gaa cag gtg aat cat gca ttg gag         720
Glu Lys Ile Gly Lys Asp Leu Ala Glu Gln Val Asn His Ala Leu Glu
225                 230                 235                 240 ctt cca ttg cat cga agg acg caa aga cta gaa gct gtt tgg agc att         768
Leu Pro Leu His Arg Arg Thr Gln Arg Leu Glu Ala Val Trp Ser Ile
                245                 250                 255 gaa gca tac cgt aaa aag gaa gat gca gat caa gta ctg cta gaa ctt         816
Glu Ala Tyr Arg Lys Lys Glu Asp Ala Asp Gln Val Leu Leu Glu Leu
            260                 265                 270 gct ata ttg gac tac aac atg att caa tca gta tac caa aga gat ctt         864
Ala Ile Leu Asp Tyr Asn Met Ile Gln Ser Val Tyr Gln Arg Asp Leu
            275                 280                 285 cgc gag aca tca agg tgg tgg agg cgt gtg ggt ctt gca aca aag ttg         912
Arg Glu Thr Ser Arg Trp Trp Arg Arg Val Gly Leu Ala Thr Lys Leu
290                 295                 300 cat ttt gct aga gac agg tta att gaa agc ttt tac tgg gca gtt gga         960
His Phe Ala Arg Asp Arg Leu Ile Glu Ser Phe Tyr Trp Ala Val Gly
305                 310                 315                 320 gtt gcg ttt gaa cct caa tac agt gat tgc cgt aat tcc gta gca aaa        1008
Val Ala Phe Glu Pro Gln Tyr Ser Asp Cys Arg Asn Ser Val Ala Lys
                325                 330                 335 atg ttt tcg ttt gta aca atc att gat gat atc tat gat gtt tat ggt        1056
Met Phe Ser Phe Val Thr Ile Ile Asp Asp Ile Tyr Asp Val Tyr Gly
            340                 345                 350 act ctg gat gag ttg gag cta ttt aca gat gct gtt gag aga tgg gat        1104
Thr Leu Asp Glu Leu Glu Leu Phe Thr Asp Ala Val Glu Arg Trp Asp
            355                 360                 365 gtt aat gcc atc gat gat ctt ccg gat tat atg aag ctc tgc ttc cta        1152
Val Asn Ala Ile Asp Asp Leu Pro Asp Tyr Met Lys Leu Cys Phe Leu
370                 375                 380 gct ctc tat aac act atc aat gag ata gct tat gat aat ctg aag gac        1200
Ala Leu Tyr Asn Thr Ile Asn Glu Ile Ala Tyr Asp Asn Leu Lys Asp
385                 390                 395                 400 aag ggg gaa aac att ctt cca tac cta aca aaa gcg tgg gca gat tta        1248
Lys Gly Glu Asn Ile Leu Pro Tyr Leu Thr Lys Ala Trp Ala Asp Leu
                405                 410                 415 tgc aat gca ttc cta caa gaa gca aaa tgg ttg tac aat aag tcc aca        1296
Cys Asn Ala Phe Leu Gln Glu Ala Lys Trp Leu Tyr Asn Lys Ser Thr
            420                 425                 430 cca aca ttt gat gaa tat ttc gga aat gca tgg aaa tca tcc tca ggg        1344
Pro Thr Phe Asp Glu Tyr Phe Gly Asn Ala Trp Lys Ser Ser Ser Gly
            435                 440                 445 cct ctt caa cta gtt ttt gcc tac ttt gcc gtt gtt caa aac atc aag        1392
Pro Leu Gln Leu Val Phe Ala Tyr Phe Ala Val Val Gln Asn Ile Lys
450                 455                 460 aaa gag gaa att gat aac tta caa aag tat cat gat atc atc agt agg        1440
Lys Glu Glu Ile Asp Asn Leu Gln Lys Tyr His Asp Ile Ile Ser Arg
465                 470                 475                 480 cct tcc cac atc ttt cgt ctt tgc aac gac ttg gct tca gca tcg gct        1488
Pro Ser His Ile Phe Arg Leu Cys Asn Asp Leu Ala Ser Ala Ser Ala
                485                 490                 495
```

```
gag ata gcg aga ggt gaa acc gcg aat tct gta tca tgc tac atg cgt     1536
Glu Ile Ala Arg Gly Glu Thr Ala Asn Ser Val Ser Cys Tyr Met Arg
            500                 505                 510 aca aaa ggc att tct gag gaa ctt gct act gaa tcc gta atg aat ttg     1584
Thr Lys Gly Ile Ser Glu Glu Leu Ala Thr Glu Ser Val Met Asn Leu
            515                 520                 525 atc gac gaa acc tgg aaa aag atg aac aaa gaa aag ctt ggt ggc tct     1632
Ile Asp Glu Thr Trp Lys Lys Met Asn Lys Glu Lys Leu Gly Gly Ser
530                 535                 540 ctg ttt gca aaa cct ttt gtc gaa aca gct att aac ctt gca cga caa     1680
Leu Phe Ala Lys Pro Phe Val Glu Thr Ala Ile Asn Leu Ala Arg Gln
545                 550                 555                 560 tcc cat tgc act tat cac aac gga gat gcg cat act tca cca gat gag     1728
Ser His Cys Thr Tyr His Asn Gly Asp Ala His Thr Ser Pro Asp Glu
                565                 570                 575 ctc act agg aaa cgt gtc ctg tca gta atc aca gag cct att cta ccc     1776
Leu Thr Arg Lys Arg Val Leu Ser Val Ile Thr Glu Pro Ile Leu Pro
            580                 585                 590 ttt gag aga taa                                                     1788
Phe Glu Arg
        595

<210> SEQ ID NO 2
<211> LENGTH: 595
<212> TYPE: PRT
<213> ORGANISM: Populus nigra

<400> SEQUENCE: 2

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Thr Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Pro Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Ala Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Lys Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Asp Leu Ala Glu Gln Val Asn His Ala Leu Glu
```

```
            225                 230                 235                 240
Leu Pro Leu His Arg Arg Thr Gln Arg Leu Glu Ala Val Trp Ser Ile
            245                 250                 255

Glu Ala Tyr Arg Lys Glu Asp Ala Asp Gln Val Leu Glu Leu
            260                 265                 270

Ala Ile Leu Asp Tyr Asn Met Ile Gln Ser Val Tyr Gln Arg Asp Leu
            275                 280                 285

Arg Glu Thr Ser Arg Trp Trp Arg Arg Val Gly Leu Ala Thr Lys Leu
            290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
            325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
            355                 360                 365

Val Asn Ala Ile Asp Asp Leu Pro Asp Tyr Met Lys Leu Cys Phe Leu
            370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
            405                 410                 415

Cys Asn Ala Phe Leu Gln Glu Ala Lys Trp Leu Tyr Asn Lys Ser Thr
            420                 425                 430

Pro Thr Phe Asp Glu Tyr Phe Gly Asn Ala Trp Lys Ser Ser Ser Gly
            435                 440                 445

Pro Leu Gln Leu Val Phe Ala Tyr Phe Ala Val Val Gln Asn Ile Lys
            450                 455                 460

Lys Glu Glu Ile Asp Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
            485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
            515                 520                 525

Ile Asp Glu Thr Trp Lys Lys Met Asn Lys Glu Lys Leu Gly Gly Ser
            530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
            565                 570                 575

Leu Thr Arg Lys Arg Val Leu Ser Val Ile Thr Glu Pro Ile Leu Pro
            580                 585                 590

Phe Glu Arg
        595

<210> SEQ ID NO 3
<211> LENGTH: 34
<212> TYPE: DNA
<213> ORGANISM: Artificial
<220> FEATURE:
<223> OTHER INFORMATION: Oligonucleotide primer for PCR
```

<400> SEQUENCE: 3

```
aggatccacc atggcaactg aattattgtg cttg                                    34
```

<210> SEQ ID NO 4
<211> LENGTH: 32
<212> TYPE: DNA
<213> ORGANISM: Artificial
<220> FEATURE:
<223> OTHER INFORMATION: Oligonucleotide primer for PCR

<400> SEQUENCE: 4

```
tcggatcctt atctctcaaa gggtagaata gg                                      32
```

<210> SEQ ID NO 5
<211> LENGTH: 1146
<212> TYPE: DNA
<213> ORGANISM: Bacillus methanolicus
<220> FEATURE:
<221> NAME/KEY: CDS
<222> LOCATION: (1)..(1146)
<223> OTHER INFORMATION:

<400> SEQUENCE: 5

```
atg aca aac ttt ttc att cca cca gcc agc gta att gga cga ggt gca         48
Met Thr Asn Phe Phe Ile Pro Pro Ala Ser Val Ile Gly Arg Gly Ala
1               5                   10                  15 gta aag gaa gta gga aca aga ctt aag caa att gga gct aag aaa gcg         96
Val Lys Glu Val Gly Thr Arg Leu Lys Gln Ile Gly Ala Lys Lys Ala
            20                  25                  30 ctt atc gtt aca gat gca ttt ctt cat agc aca ggt tta tct gaa gaa        144
Leu Ile Val Thr Asp Ala Phe Leu His Ser Thr Gly Leu Ser Glu Glu
        35                  40                  45 gtt gct aaa aac att cgt gaa gct ggc ctt gat gtt gcg att ttc cca        192
Val Ala Lys Asn Ile Arg Glu Ala Gly Leu Asp Val Ala Ile Phe Pro
    50                  55                  60 aaa gct caa cca gat cca gca gat aca caa gtt cat gaa ggt gta gat        240
Lys Ala Gln Pro Asp Pro Ala Asp Thr Gln Val His Glu Gly Val Asp
65                  70                  75                  80 gta ttc aaa caa gaa aac tgt gat gca ctt gtt tct atc ggt gga ggt        288
Val Phe Lys Gln Glu Asn Cys Asp Ala Leu Val Ser Ile Gly Gly Gly
                85                  90                  95 agc tct cac gat aca gct aaa gca atc ggt tta gtt gca gca aac ggc        336
Ser Ser His Asp Thr Ala Lys Ala Ile Gly Leu Val Ala Ala Asn Gly
            100                 105                 110 gga aga atc aat gac tat caa ggt gta aac agt gta gaa aaa cca gtc        384
Gly Arg Ile Asn Asp Tyr Gln Gly Val Asn Ser Val Glu Lys Pro Val
        115                 120                 125 gtt cca gta gtt gca atc act aca aca gct ggt act ggt agt gaa aca        432
Val Pro Val Val Ala Ile Thr Thr Thr Ala Gly Thr Gly Ser Glu Thr
    130                 135                 140 aca tct ctt gca gtt att aca gac tct gca cgt aaa gta aaa atg cct        480
Thr Ser Leu Ala Val Ile Thr Asp Ser Ala Arg Lys Val Lys Met Pro
145                 150                 155                 160 gtt att gat gag aaa att act cca act gta gca att gtt gac cca gaa        528
Val Ile Asp Glu Lys Ile Thr Pro Thr Val Ala Ile Val Asp Pro Glu
                165                 170                 175 tta atg gtg aaa aaa cca gct gga tta aca atc gca act ggt atg gac        576
Leu Met Val Lys Lys Pro Ala Gly Leu Thr Ile Ala Thr Gly Met Asp
            180                 185                 190 gca tta tca cac gca att gaa gca tat gtt gca aaa ggt gct aca cca        624
Ala Leu Ser His Ala Ile Glu Ala Tyr Val Ala Lys Gly Ala Thr Pro
        195                 200                 205
```

```
gtt act gat gca ttt gca att caa gca atg aaa ctc atc aat gaa tac      672
Val Thr Asp Ala Phe Ala Ile Gln Ala Met Lys Leu Ile Asn Glu Tyr
    210                 215                 220 tta cca aaa gcg gtg gca aac gga gaa gac atc gaa gca cgt gaa gca      720
Leu Pro Lys Ala Val Ala Asn Gly Glu Asp Ile Glu Ala Arg Glu Ala
225                 230                 235                 240 atg gct tat gca caa tac atg gca gga gtg gca ttt aac aac ggt ggt      768
Met Ala Tyr Ala Gln Tyr Met Ala Gly Val Ala Phe Asn Asn Gly Gly
                245                 250                 255 tta gga tta gta cac tct att tct cac caa gta ggt gga gtt tac aaa      816
Leu Gly Leu Val His Ser Ile Ser His Gln Val Gly Gly Val Tyr Lys
            260                 265                 270 tta caa cac gga atc tgt aac tca gtt aat atg cca cac gtt tgc gca      864
Leu Gln His Gly Ile Cys Asn Ser Val Asn Met Pro His Val Cys Ala
        275                 280                 285 ttc aac cta att gct aaa act gag cgc ttc gca cac att gct gag ctt      912
Phe Asn Leu Ile Ala Lys Thr Glu Arg Phe Ala His Ile Ala Glu Leu
    290                 295                 300 tta ggc gag aat gtt tct ggc tta agc act gca gca gct gct gag aga      960
Leu Gly Glu Asn Val Ser Gly Leu Ser Thr Ala Ala Ala Ala Glu Arg
305                 310                 315                 320 gca att gta gcg ctt gaa cgc tat aac aaa aac ttc ggt atc cca tct     1008
Ala Ile Val Ala Leu Glu Arg Tyr Asn Lys Asn Phe Gly Ile Pro Ser
                325                 330                 335 ggc tat gca gaa atg ggc gtg aaa gaa gag gat atc gaa tta tta gcg     1056
Gly Tyr Ala Glu Met Gly Val Lys Glu Glu Asp Ile Glu Leu Leu Ala
            340                 345                 350 aaa aac gca ttc gaa gac gta tgt act caa agc aac cca cgt gtt gct     1104
Lys Asn Ala Phe Glu Asp Val Cys Thr Gln Ser Asn Pro Arg Val Ala
        355                 360                 365 aca gtt caa gac att gca caa atc atc aaa aac gct ctg taa             1146
Thr Val Gln Asp Ile Ala Gln Ile Ile Lys Asn Ala Leu
    370                 375                 380

<210> SEQ ID NO 6
<211> LENGTH: 381
<212> TYPE: PRT
<213> ORGANISM: Bacillus methanolicus

<400> SEQUENCE: 6

Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Thr Ala Gly Thr Gly Ser Glu Thr
    130                 135                 140
```

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
            165                 170                 175

Leu Met Val Lys Lys Pro Ala Gly Leu Thr Ile Ala Thr Gly Met Asp
        180                 185                 190

Ala Leu Ser His Ala Ile Glu Ala Tyr Val Ala Lys Gly Ala Thr Pro
            195                 200                 205

Val Thr Asp Ala Phe Ala Ile Gln Ala Met Lys Leu Ile Asn Glu Tyr
210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly
                245                 250                 255

Leu Gly Leu Val His Ser Ile Ser His Gln Val Gly Gly Val Tyr Lys
            260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
    290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Asp Ile Glu Leu Leu Ala
            340                 345                 350

Lys Asn Ala Phe Glu Asp Val Cys Thr Gln Ser Asn Pro Arg Val Ala
        355                 360                 365

Thr Val Gln Asp Ile Ala Gln Ile Ile Lys Asn Ala Leu
    370                 375                 380

<210> SEQ ID NO 7
<211> LENGTH: 45
<212> TYPE: DNA
<213> ORGANISM: Artificial
<220> FEATURE:
<223> OTHER INFORMATION: Oligonucleotide primer for PCR

<400> SEQUENCE: 7
acagatctgg tcttgtaaac atgacaaact ttttcattcc accag         45

<210> SEQ ID NO 8
<211> LENGTH: 65
<212> TYPE: DNA
<213> ORGANISM: Artificial
<220> FEATURE:
<223> OTHER INFORMATION: Oligonucleotide primer for PCR

<400> SEQUENCE: 8
acggatcctc aaatgtttta agtattgttt atttaagaat tacagagcgt ttttgatgat    60
ttgtg                                                               65

<210> SEQ ID NO 9
<211> LENGTH: 630
<212> TYPE: DNA
<213> ORGANISM: Methylomonas aminofaciens
<220> FEATURE:
<221> NAME/KEY: CDS

<222> LOCATION: (1)..(630)
<223> OTHER INFORMATION:

<400> SEQUENCE: 9

| | | | | | | | | | | | | | | | | |
|---|---|---|---|---|---|---|---|---|---|---|---|---|---|---|---|---|
| atg | gca | ttg | aca | caa | atg | gca | tta | gat | tca | ctg | gat | ttc | gac | gca | act | 48 |
| Met | Ala | Leu | Thr | Gln | Met | Ala | Leu | Asp | Ser | Leu | Asp | Phe | Asp | Ala | Thr | |
| 1 | | | | 5 | | | | | 10 | | | | | 15 | | |
| gtt | gcg | ctg | gct | gaa | aag | gta | gct | cca | cac | gtt | gac | att | ctt | gaa | atc | 96 |
| Val | Ala | Leu | Ala | Glu | Lys | Val | Ala | Pro | His | Val | Asp | Ile | Leu | Glu | Ile | |
| | | | 20 | | | | | 25 | | | | | 30 | | | |
| ggt | aca | cca | tgc | atc | aag | cac | aac | ggt | atc | aag | ttg | ctg | gaa | act | ctg | 144 |
| Gly | Thr | Pro | Cys | Ile | Lys | His | Asn | Gly | Ile | Lys | Leu | Leu | Glu | Thr | Leu | |
| | | 35 | | | | | 40 | | | | | 45 | | | | |
| cgc | gca | aag | ttc | cct | aac | aac | aag | atc | ctg | gtt | gac | ctg | aag | act | atg | 192 |
| Arg | Ala | Lys | Phe | Pro | Asn | Asn | Lys | Ile | Leu | Val | Asp | Leu | Lys | Thr | Met | |
| 50 | | | | | 55 | | | | | 60 | | | | | | |
| gat | gct | ggc | ttc | tac | gaa | gct | gag | cct | ttc | tac | aag | gct | ggt | gct | gat | 240 |
| Asp | Ala | Gly | Phe | Tyr | Glu | Ala | Glu | Pro | Phe | Tyr | Lys | Ala | Gly | Ala | Asp | |
| 65 | | | | | 70 | | | | | 75 | | | | | 80 | |
| atc | act | acc | gtt | ctg | ggc | gta | gct | gat | ctg | ggt | aca | atc | aaa | ggc | gta | 288 |
| Ile | Thr | Thr | Val | Leu | Gly | Val | Ala | Asp | Leu | Gly | Thr | Ile | Lys | Gly | Val | |
| | | | | 85 | | | | | 90 | | | | | 95 | | |
| atc | gac | gct | gct | aac | aag | tac | ggc | aag | aag | gca | cag | atc | gac | ctg | atc | 336 |
| Ile | Asp | Ala | Ala | Asn | Lys | Tyr | Gly | Lys | Lys | Ala | Gln | Ile | Asp | Leu | Ile | |
| | | | 100 | | | | | 105 | | | | | 110 | | | |
| aat | gtt | ggt | gat | aag | gct | gct | cgt | act | aag | gaa | gtt | gct | aag | ctg | ggc | 384 |
| Asn | Val | Gly | Asp | Lys | Ala | Ala | Arg | Thr | Lys | Glu | Val | Ala | Lys | Leu | Gly | |
| | | 115 | | | | | 120 | | | | | 125 | | | | |
| gcg | cac | atc | att | ggc | gtt | cac | act | ggt | ctg | gac | caa | caa | gct | gct | ggt | 432 |
| Ala | His | Ile | Ile | Gly | Val | His | Thr | Gly | Leu | Asp | Gln | Gln | Ala | Ala | Gly | |
| 130 | | | | | 135 | | | | | 140 | | | | | | |
| caa | act | cct | ttt | gct | gac | ctg | gca | act | gta | act | ggc | ctg | aac | ctg | ggt | 480 |
| Gln | Thr | Pro | Phe | Ala | Asp | Leu | Ala | Thr | Val | Thr | Gly | Leu | Asn | Leu | Gly | |
| 145 | | | | | 150 | | | | | 155 | | | | | 160 | |
| ctg | gaa | gtt | tcc | gta | gct | ggt | ggt | gtt | aag | cct | gct | act | gtt | gca | caa | 528 |
| Leu | Glu | Val | Ser | Val | Ala | Gly | Gly | Val | Lys | Pro | Ala | Thr | Val | Ala | Gln | |
| | | | | 165 | | | | | 170 | | | | | 175 | | |
| gtt | aaa | gac | gct | ggt | gct | acc | atc | atc | gtc | gct | ggc | gct | gct | atc | tac | 576 |
| Val | Lys | Asp | Ala | Gly | Ala | Thr | Ile | Ile | Val | Ala | Gly | Ala | Ala | Ile | Tyr | |
| | | | 180 | | | | | 185 | | | | | 190 | | | |
| ggt | gct | gct | gac | cca | gct | gct | gct | gct | gaa | atc | act | ggc | ctg | gct | | 624 |
| Gly | Ala | Ala | Asp | Pro | Ala | Ala | Ala | Ala | Glu | Ile | Thr | Gly | Leu | Ala | | |
| | | 195 | | | | | 200 | | | | | 205 | | | | |
| aag | taa | | | | | | | | | | | | | | | 630 |
| Lys | | | | | | | | | | | | | | | | |

<210> SEQ ID NO 10
<211> LENGTH: 209
<212> TYPE: PRT
<213> ORGANISM: Methylomonas aminofaciens

<400> SEQUENCE: 10

Met Ala Leu Thr Gln Met Ala Leu Asp Ser Leu Asp Phe Asp Ala Thr
1               5                   10                  15

Val Ala Leu Ala Glu Lys Val Ala Pro His Val Asp Ile Leu Glu Ile
            20                  25                  30

Gly Thr Pro Cys Ile Lys His Asn Gly Ile Lys Leu Leu Glu Thr Leu
        35                  40                  45

Arg Ala Lys Phe Pro Asn Asn Lys Ile Leu Val Asp Leu Lys Thr Met
50                  55                  60

```
Asp Ala Gly Phe Tyr Glu Ala Glu Pro Phe Tyr Lys Ala Gly Ala Asp
 65                  70                  75                  80

Ile Thr Thr Val Leu Gly Val Ala Asp Leu Gly Thr Ile Lys Gly Val
                 85                  90                  95

Ile Asp Ala Ala Asn Lys Tyr Gly Lys Lys Ala Gln Ile Asp Leu Ile
            100                 105                 110

Asn Val Gly Asp Lys Ala Ala Arg Thr Lys Glu Val Ala Lys Leu Gly
            115                 120                 125

Ala His Ile Ile Gly Val His Thr Gly Leu Asp Gln Gln Ala Ala Gly
        130                 135                 140

Gln Thr Pro Phe Ala Asp Leu Ala Thr Val Thr Gly Leu Asn Leu Gly
145                 150                 155                 160

Leu Glu Val Ser Val Ala Gly Gly Val Lys Pro Ala Thr Val Ala Gln
                165                 170                 175

Val Lys Asp Ala Gly Ala Thr Ile Ile Val Gly Ala Ala Ile Tyr
            180                 185                 190

Gly Ala Ala Asp Pro Ala Ala Ala Ala Glu Ile Thr Gly Leu Ala
        195                 200                 205

Lys
```

```
<210> SEQ ID NO 11
<211> LENGTH: 33
<212> TYPE: DNA
<213> ORGANISM: Artificial
<220> FEATURE:
<223> OTHER INFORMATION: Oligonucleotide primer for PCR

<400> SEQUENCE: 11
acagatctat ggcattgaca caaatggcat tag                            33

<210> SEQ ID NO 12
<211> LENGTH: 63
<212> TYPE: DNA
<213> ORGANISM: Artificial
<220> FEATURE:
<223> OTHER INFORMATION: Oligonucleotide primer for PCR

<400> SEQUENCE: 12
tcggatcctc aaatgtttta agtattgttt atttaagaat tacttagcca ggccagtgat   60
ttc                                                                63

<210> SEQ ID NO 13
<211> LENGTH: 546
<212> TYPE: DNA
<213> ORGANISM: Methylomonas aminofaciens
<220> FEATURE:
<221> NAME/KEY: CDS
<222> LOCATION: (1)..(546)
<223> OTHER INFORMATION:

<400> SEQUENCE: 13 atg aac aaa tat caa gag ctc gtg gtc agc aag ctg acc aat gtt atc     48
Met Asn Lys Tyr Gln Glu Leu Val Val Ser Lys Leu Thr Asn Val Ile
1               5                  10                  15 aat aac act gca gaa ggc tat gac gac aag att ttg agt cta gtc gat     96
Asn Asn Thr Ala Glu Gly Tyr Asp Asp Lys Ile Leu Ser Leu Val Asp
            20                  25                  30 gca gcc ggc cgt aca ttt atc ggt ggt gct ggc cgt tcc ttg ctg gtt    144
Ala Ala Gly Arg Thr Phe Ile Gly Gly Ala Gly Arg Ser Leu Leu Val
        35                  40                  45
```

```
tcc cgt ttc ttt gca atg cgc ttg gtg cat gca ggt tac caa gtt agc      192
Ser Arg Phe Phe Ala Met Arg Leu Val His Ala Gly Tyr Gln Val Ser
    50                  55                  60 atg gtc ggt gaa gtt gtt act cca agt atc caa gct ggt gat ctt ttc      240
Met Val Gly Glu Val Val Thr Pro Ser Ile Gln Ala Gly Asp Leu Phe
65                  70                  75                  80 att gtg atc tct ggc tct ggc agc aca gaa acc ctg atg cct ttg gtt      288
Ile Val Ile Ser Gly Ser Gly Ser Thr Glu Thr Leu Met Pro Leu Val
                85                  90                  95 aag aag gca aag agc caa ggt gcc aag att atc gtg att tcc atg aag      336
Lys Lys Ala Lys Ser Gln Gly Ala Lys Ile Ile Val Ile Ser Met Lys
            100                 105                 110 gct cag tcc cca atg gct gaa ttg gct gat ctg gtt gtg cca gtt ggt      384
Ala Gln Ser Pro Met Ala Glu Leu Ala Asp Leu Val Val Pro Val Gly
        115                 120                 125 ggc aac gat gcc aat gca ttt gac aag act cat ggt atg cct atg ggt      432
Gly Asn Asp Ala Asn Ala Phe Asp Lys Thr His Gly Met Pro Met Gly
130                 135                 140 act att ttc gag ttg tcc acc ctg tgg ttc ctc gaa gcg act att gcc      480
Thr Ile Phe Glu Leu Ser Thr Leu Trp Phe Leu Glu Ala Thr Ile Ala
145                 150                 155                 160 aag ctg gta gat caa aaa ggt ctg aca gaa gaa ggt atg cgc gcg att      528
Lys Leu Val Asp Gln Lys Gly Leu Thr Glu Glu Gly Met Arg Ala Ile
                165                 170                 175 cat gct aac ctc gag taa                                              546
His Ala Asn Leu Glu
            180

<210> SEQ ID NO 14
<211> LENGTH: 181
<212> TYPE: PRT
<213> ORGANISM: Methylomonas aminofaciens

<400> SEQUENCE: 14

Met Asn Lys Tyr Gln Glu Leu Val Val Ser Lys Leu Thr Asn Val Ile
1               5                   10                  15

Asn Asn Thr Ala Glu Gly Tyr Asp Asp Lys Ile Leu Ser Leu Val Asp
            20                  25                  30

Ala Ala Gly Arg Thr Phe Ile Gly Gly Ala Gly Arg Ser Leu Leu Val
        35                  40                  45

Ser Arg Phe Phe Ala Met Arg Leu Val His Ala Gly Tyr Gln Val Ser
    50                  55                  60

Met Val Gly Glu Val Val Thr Pro Ser Ile Gln Ala Gly Asp Leu Phe
65                  70                  75                  80

Ile Val Ile Ser Gly Ser Gly Ser Thr Glu Thr Leu Met Pro Leu Val
                85                  90                  95

Lys Lys Ala Lys Ser Gln Gly Ala Lys Ile Ile Val Ile Ser Met Lys
            100                 105                 110

Ala Gln Ser Pro Met Ala Glu Leu Ala Asp Leu Val Val Pro Val Gly
        115                 120                 125

Gly Asn Asp Ala Asn Ala Phe Asp Lys Thr His Gly Met Pro Met Gly
130                 135                 140

Thr Ile Phe Glu Leu Ser Thr Leu Trp Phe Leu Glu Ala Thr Ile Ala
145                 150                 155                 160

Lys Leu Val Asp Gln Lys Gly Leu Thr Glu Glu Gly Met Arg Ala Ile
                165                 170                 175

His Ala Asn Leu Glu
```

180

```
<210> SEQ ID NO 15
<211> LENGTH: 44
<212> TYPE: DNA
<213> ORGANISM: Artificial
<220> FEATURE:
<223> OTHER INFORMATION: Oligonucleotide primer for PCR

<400> SEQUENCE: 15
acagatctgg tcttgtaaac atgaacaaat atcaagagct cgtg           44

<210> SEQ ID NO 16
<211> LENGTH: 63
<212> TYPE: DNA
<213> ORGANISM: Artificial
<220> FEATURE:
<223> OTHER INFORMATION: Oligonucleotide primer for PCR

<400> SEQUENCE: 16
tcggatcctc aaatgtttta agtattgttt atttaagaat tactcgaggt tagcatgaat   60
cgc                                                         63

<210> SEQ ID NO 17
<211> LENGTH: 45
<212> TYPE: DNA
<213> ORGANISM: Artificial
<220> FEATURE:
<223> OTHER INFORMATION: Oligonucleotide primer for PCR

<400> SEQUENCE: 17
acggatccgg tcttgtaaac atggcaactg aattattgtg cttgc           45

<210> SEQ ID NO 18
<211> LENGTH: 32
<212> TYPE: DNA
<213> ORGANISM: Artificial
<220> FEATURE:
<223> OTHER INFORMATION: Oligonucleotide primer for PCR

<400> SEQUENCE: 18
tgcccgggtt atctctcaaa gggtagaata gg                         32

<210> SEQ ID NO 19
<211> LENGTH: 31
<212> TYPE: DNA
<213> ORGANISM: Artificial
<220> FEATURE:
<223> OTHER INFORMATION: Oligonucleotide primer for PCR

<400> SEQUENCE: 19
aggatccatg gcaactgaat tattgtgctt g                          31

<210> SEQ ID NO 20
<211> LENGTH: 39
<212> TYPE: DNA
<213> ORGANISM: Artificial
<220> FEATURE:
<223> OTHER INFORMATION: Oligonucleotide primer for PCR

<400> SEQUENCE: 20
tggtacctta ttcttttatc tctcaaaggg tagaatagg                  39

<210> SEQ ID NO 21
<211> LENGTH: 62
```

```
<212> TYPE: DNA
<213> ORGANISM: Artificial
<220> FEATURE:
<223> OTHER INFORMATION: Oligonucleotide primer for PCR

<400> SEQUENCE: 21
cgggtaccaa ttttgttaat aattcaggga gggattctaa atgactcttc cgacctcggt      60
gg                                                                    62

<210> SEQ ID NO 22
<211> LENGTH: 71
<212> TYPE: DNA
<213> ORGANISM: Artificial
<220> FEATURE:
<223> OTHER INFORMATION: Oligonucleotide primer for PCR

<400> SEQUENCE: 22
aggtaccatt aaaaaaataa gagttaccat ttaaggtaac tcttattttt atcagcacgc      60
tcggtagagg c                                                          71

<210> SEQ ID NO 23
<211> LENGTH: 6440
<212> TYPE: DNA
<213> ORGANISM: Streptomyces griseolosporeus

<400> SEQUENCE: 23
atgactcttc cgacctcggt ggaggaggga tcgaaggccc accgggctcg cgccgtcggc      60
accggtcgcg ctcatgccaa ggccattctg ctgggagagc acgcggtcgt gtacggaacc     120
ccggcgctcg cgatgcccat tccccaactc gcggtcacgg caagcgccgg ctggtccggc     180
cgatccgccg agagccgggg cggtccgacc ttcaccatga ccgggtcggc ttcccgcgcg     240
gtcacggcac aggccttgga cggtctgcga cgtctgaccg cctcggtcaa ggcgcacacg     300
ggagtgaccg acgacaaaca cctcgacgtc agcctcgacg gggcgattcc gcccggccgc     360
gggctcggct ccagcgccgc gaacgcacga gcgatcatcc tcgccctggc cgacctcttc     420
ggccgggagc tgaccgaggg cgaggtgttc gacctggtgc aggaggccga gaacctgacg     480
cacggccggg ccagcggcgt cgacgccgtg accgtcggcg ccaccgcccc gctcctcttc     540
cgggcgggca cggcacaggc gctggacatc ggctgcgacg cactgttcgt cgtcgcggac     600
agcggaaccg cagggagcac caaggaggcg atcgagctgc ttcgcgccgg attccggggcc     660 ggggccggaa aggaggaacg gttcatgcac cgtgccgcgc acctcgtcga cgatgccagg     720
gcctccctcg ccgagggcga acccgaggcg ttcggatcgt gcctgaccga gtatcacggc     780
ctgctgcgcg gggcgggtct gagcaccgac cggatcgatg cactggtgga tgccgcgctg     840
caggccgaca gcctgggcgc caagatcacc ggtggcggtc tgggcggttg tgttctcgcg     900
atgtcccgcc cggagcgggc cgaggaagtg gcccggcagc tgcacgccgc cggcgccgta     960
cgcacgtggg ccgtacagct gaggaggtcc actcatgagc gctgaacagc cgtcaaccct    1020
gctgtccgcg ccgcgacgga caccgcgaca gccgttgccc agccgaacat cgcgctgatc    1080
aagtactggg gcaagaagga cgagcacctg gtcctgcccc gtaccgacag cctgtcgatg    1140
actctggaca tcttcccgac gaccaccccg gtccagctcg cgcccggcgc cgggcaggac    1200
acggtggcct tcaacggcga gcccgcgacg ggagaggccg agcggcgcat caccgcattc    1260
ctccggctgg tgcgggagcg gtcggggcgc accgaacggg cccgcgtcga gacgagaaac    1320 accgtccca ccggggccgg cctggcctcg tcggccagcg gtttcgctgc cctcgccgtc    1380
```

```
gccgccgccg cggcgtacgg gctcggtctc gacgcgcggg gcctgtcccg gctggcccga    1440
cgcggctccg ggtcggcctc ccggtcgatc ttcgacgggt tcgccgtgtg cacgccggc     1500 cacgccggcg gcactcccga ggaggccgat ctcggctcgt acgccgaacc ggtgccggcc    1560
gtggacctgg agccggcgct ggtggtcgcg gtggtcagcg ccgccccaa ggcggtgtcc     1620 agccgggagg ccatgcggag gaccgtggac acctcaccgc tgtacgagcc gtgggcggtg   1680
tccagccggg ccgacctggc ggacatcgga gccgcgctcg cccgcggcaa cctgccggcg    1740
gtgggcgaga tcgcggagcg caacgccctc ggcatgcacg ccaccatgct ggccgcacgc    1800
cccgccgtgc gctacctgtc accggcctcg ctcgccgtgc tcgacggcgt tctgcagttg    1860
cggcgggacg gcgtgccggc ctacgcgacg atggacgccg gtcccaacgt gaaggtgctc    1920
tgcccgcgtt cggacgccga gcgggtcgcg gaagccctgc gcgccgccgc gccggtcgga    1980
gcggtgcaca tcgccggtcc ggggcggggt gcccgcctgg tggcggagga atgccggtga    2040
ccggcccgcg cgcggtgacc cggcgcgccc cgggcaagct cttcgtcgcg ggtgaatacg    2100
cggtggtgga accgggcaac cgggcgatcc tggtggcagt cgaccggtac gtcaccgtca    2160
ccgtgtccga cggcgccgca cccggtgtcg tcgtctcctc cgacatcgga gccggcccgg    2220
tgcaccaccc gtggcaggac gggcggctga caggcggtac gggcacacct catgtggtgg    2280
cggcggtcga ccgtggcc cgcctcctgg ccgaacgcgg ccggtccgtc cgccgttgg     2340 ggtggtcgat cagcagcacg ctgcacgagg acggccggaa gttcggactg gctccagcg    2400 gcgcggtgac ggtggcgacg gtcagtgccg tcgcagccca ttgcggactg gaactcaccg    2460
ccgaagaacg cttccggacg gcgctgatcg cctccgcccg catcgacccc aggggatccg    2520
gcggagacat cgccaccagc acctgggggcg gctggatcgc ctaccgggcg cccgaccggg    2580
acgccgtact cgacttgacc cgccgtcagg gggtcgacga ggcactccgg gcgccgtggc    2640
cgggcttctc cgtacgactg tcgccgcccc ggaacctctg cctcgaggtc ggctggaccg    2700 gcaacccccgt gtccaccacg tccctcctga cggacctgca tcggcgcacc tggcgggca    2760 gccccgcgta ccggaggtac gtcggggcga ccggcgagct cgtggacgcc gcagtcatcg    2820
cgctggagga cggcgacacc gagggcctgt tgcggcaggt ccggcgggcc cgtcacgaga    2880
tggtccgcct cgacgacgag gtcggcctcg gcatcttcac ccccgaactg acggccctct    2940
gcgccatcgc cgaacgcgcc ggcgcggcca agccctcggg ggccggggc ggcgactgcg    3000 gcatcgcgct gctggacgcc gaggcccgct acgaccgctc accgttgcac cggcaatggg    3060
ccgcggccgg ggtgctgccg ctactggtgt cgcctgccac ggaaggagtc gaggaatgag    3120
cagtgcccag cgcaaggacg accatgtccg gctcgccacg gagcagcagc gcgcgcacag    3180
cggacgcaac cagttcgacg acgtgtcgtt cgtccaccac gccctcgccg gaatcgaccg    3240
gccggacgtc cgcctggcca cgacgttcgc cggcatcacc tggcgactgc cgctgtacat    3300
caacgcgatg acgggcggca cgccaagac cggcgccatc aaccgggacc tggccgtcgc    3360
cgccagggag accggcgccg ccatcgcgtc cgggtccatg cacgcctttt tcagggaccc    3420
ctcctgcgcg gacaccttcc gcgtgctgcg caccgagaac cccgacggtt tcgtgatggc    3480
gaacgtcaac gcgaccgcgt ccgtcgacaa cgcccgccgg gccgtcgacc tgatcgaggc    3540
gaacgccctg cagatccacc tgaacacggc gcaggagacg cccatgccgg agggcgaccg    3600
gtcgttcggg tcgtggccgg cccagatcgc gaagatcacg gcggccgtcg acgtcccggt    3660
gatcgtcaag gaggtcggca acgggctcag caggcagacc ctcctggcgc tgccggatct    3720
gggggtccgg gtcgccgacg tcagcggccg cggcggcacc gacttcgccc gtatcgagaa    3780
```

```
cagccggcgc ccccctgggcg actacgcctt cctgcacggc tggggcagt ccaccccggc    3840 ctgtctgctg gacgctcagg acgtcggctt ccccctgctg gcctccggtg ggatccgcaa    3900
cccgctcgac gtcgcccggg cgctcgcgct cggcgccggc gccgtgggct cctcgggcgt    3960
attcctgcgc acgctgatcg acgggggcgt atccgccctg gtcgcacaga tctccacctg    4020
gctggaccag ctcgccgcgc tgcagaccat gctcggtgcg cggaccccg ccgacctcac    4080 ccgctgcgac gtgctgatcc acggcccgct ccggtccttc tgcacggacc ggggcataga    4140
catcgggcgg ttcgcccggc gcagcagctc cgccgacatc cgttccgaga tgacaggaag    4200
cacacgatga ccgaagcgca cgccaccgcc ggcgtcccga tgcggtgggt ggggcccgtc    4260
cgcatctcgg gaaacgtcgc caccatcgaa acccaggtgc cgctggccac gtacgagtct    4320
ccgctctggc cttcggtggg ccgcggccgcg aaggtgtccc ggctgaccga aagggcatc    4380 gtcgccacgc tcgtcgacga gcgcatgacc cgttccgtgc tcgtcgaggc gaccgacgcg    4440
ctcaccgcgc tctccgcggc acggaccatc gaggcccgca tcgacgagct gcgcgagctg    4500
gtgcgcggct gcagccggtt cgcccagctg atcggcatcc ggcacgagat caccggaaac    4560
ctgctgttcg tccggttcga gttcagcacc ggtgacgcct ccgggcacaa catgcgacc    4620 ctggcttccg acgtgctcct ccagcatctg ctggaaacgg ttcccggcat ctcctacggg    4680
tcgatctccg ggaactactg cacggacaag aaggccaccg ccatcaacgg catcctgggc    4740
cgcggcaaga acgtcgtcac cgagctgctc gtgccgcgtg acgtggtggc cgacgtcctg    4800
aacaccaccg ccgcgaagat cgccgagctg aacctccgca agaacctgct cgggacactt    4860
ctcgcaggcg gcatccggtc ggcgaacgcc cactacgcga acatgctgct cgcgttctac    4920
ctggcgaccg tcaggacgc ggcgaacatc gtcgagggct cccagggcgt cgtcacggcc    4980
gaggaccgcg acggcgacct ctacttagcc tgcacactgc cgaacctcat cgtcggcacg    5040
gttggcaacg gcaagggcct gggcttcgtg gagaccaacc tgaaccggct cggctgccgt    5100
gcggaccgcg agcccggcga gaacgcccgc cggctcgccg tcatcgcggc ggccacggtg    5160
ctctgcgggg agctgtcgct gctcgcggcg cagaccaacc ccggcgaact gatgcgtgcg    5220
catgtccaac tggaacgagg ccacacgacc gcgaaggctg gtgtctagag catgcccctc    5280
gccataggca tccatgatct gtcgttcgcc accggcgagt tcggctgccg cacaccgccc    5340
tcgccgctca aacggaacc gagatcggca agtaccacgc gggcatcggc caggagtcga    5400
tgagcgtccc ggccgccgac gaggacatcg tgaccctggc cgcgacggct gccgcaccga    5460
tcgtcgcccg gcacggcagc gaccggatcc gcacggtcgt gctcgcgacc gaatcgtcga    5520
tcgaccaggc gaagtcggcc ggtgtgtacg tccactccct gctcggactg ccgtcggcca    5580
cccgcgtcgt ggagctgaag caggcctgtt acggggccac ggccggcctg cagttcgcca    5640
tcggtctggt gcagcgcgac cccgcccagc aggttctcgt catcgccagt gacgtctcca    5700
agtacgacct ggacagcccc ggtgaggcga cgcaggcgc cgccgcgtc gccatgctcg    5760 taggcgccga tccggggctg gtgcggatcg aggatccgtc gggcctgttc accgtcgacg    5820
tcatggactt ctggcggccg aactaccgca ccacggctct ggtcgacggc caggaatcca    5880
tcggcgccta cctccaggcg gtggaggggg cctggaagga ctactcggag cggggcggcc    5940
actccctgga gcagttcgcc gcgttctgct accaccagcc gttcaccaag atggctcaca    6000
aggcccaccg gcacctgctg aactactgca gccacgacat ccaccacgac gacgtcacgc    6060
gtgccgtcgg ccggaccacc gcctacaaca gggtgatcgg gaacagctac accgcgtccg    6120
```

-continued

| | |
|---|---|
| tctacctggg cctcgccgcg ctcctcgacc aggccgacga cctgaccggt gagcgcatcg | 6180 |
| gattcctcag ctacggttcc ggcagcgtcg ccgagttctt cggcgggatc gtcgtcgccg | 6240 |
| gataccggga ccggctgcgg acggcggcga acatcgaggc cgtctcccgg cgacggccca | 6300 |
| tcgactacgc cggctaccgc gagctgcacg agtgggcctt ccccgcccga cggggagccc | 6360 |
| actccacccc gcagcagacc acgggaccgt tccggctgtc cggtatcagc ggccacaagc | 6420 |
| gcctctaccg agcgtgctga | 6440 |

```
<210> SEQ ID NO 24
<211> LENGTH: 75
<212> TYPE: DNA
<213> ORGANISM: Artificial
<220> FEATURE:
<223> OTHER INFORMATION: Oligonucleotide primer for PCR

<400> SEQUENCE: 24
```

| | |
|---|---|
| aggtaccatt aaaaaaataa gagttaccat ttaaggtaac tcttattttt attatctctc | 60 |
| aaagggtaga atagg | 75 |

```
<210> SEQ ID NO 25
<211> LENGTH: 2462
<212> TYPE: DNA
<213> ORGANISM: Artificial
<220> FEATURE:
<223> OTHER INFORMATION: Gene cluster containing Escherichia coli IDI
      gene and Populus nigra IspS gene

<400> SEQUENCE: 25
```

| | |
|---|---|
| ggatccatgc aaactgaaca tgttatttta ttgaatgcac agggagttcc tactggtact | 60 |
| ctggaaaagt atgccgcaca tacagcagac acccgcttac atctcgcttt ctccagttgg | 120 |
| ctgtttaatg ccaaaggaca attattagtt accgaagag cactgagcaa aaaagcatgg | 180 |
| cctggcgtgt ggactaactc tgtttgtggg catccacaac tgggagaaag caacgaagac | 240 |
| gcagtgatca gaagatgtcg ttatgagctt ggcgtggaaa ttactcctcc tgaatctatc | 300 |
| tatcctgact ttagatacag agccaccgat cctagtggca ttgtggaaaa tgaagtgtgt | 360 |
| cctgtatttg ccgcaagaac cactagtgca ttacagatca atgatgatga agtgatggat | 420 |
| tatcaatggt gtgatttagc agatgtatta catggtattg atgccactcc ttgggctttc | 480 |
| agtccttgga tggtgatgca ggcaacaaat agagaagcca gaaaaagatt atctgcattt | 540 |
| acccagctta ataattaat aattaattcg aacagaaaaa ataagtattt atataacggt | 600 |
| taattgtaag gagggttttt tatggcaact gaattattgt gtttgcatag accaatctca | 660 |
| ctgacacata aattgttcag aaatcctttg cctaaagtta tccaggccac tccttaact | 720 |
| ttgaaactta gatgttctgt aagcacagaa acgtaagct tcacagaaac agaaacagaa | 780 |
| accagaaggt ctgccaatta tgaaccaaat agctgggatt atgattattt gctgtcttct | 840 |
| gacactgacg aatctattga agtatacaaa gacaaggcca aaaagctgga ggctgaggtg | 900 |
| agaagagaga ttaacaatga aaaggcagag ttttgactc tgcctgaact gatagataat | 960 |
| gttcaaaggt taggattagg ttacagattc gagagtgaca taaggagagc ccttgataga | 1020 |
| tttgttctt caggaggatt tgatgctgtt acaaaaacta gccttcatgc tactgctctt | 1080 |
| agcttcaggc ttctcagaca gcatggcttt gaggtatctc aagaagcttt cagcggattc | 1140 |
| aaggatcaaa atgcaatttt cttgaaaaac cttaaggagg acatcaaggc aatactaagc | 1200 |
| ctatatgaag cttcatttct tgccttagaa ggagaaaata tcttggatga ggccaaggtg | 1260 |

```
tttgcaatat cacatctaaa agagcttagc gaagaaaaga ttggaaaaga cctggccgaa    1320
caggtgaatc atgcattgga gcttccattg catagaagga cacaaagact agaagctgtt    1380
tggagcattg aagcatacag aaaaaaggaa gatgcagatc aagtactgct agaacttgct    1440
atattggact acaacatgat tcaatcagta taccaaagag atcttagaga gacatcaagg    1500
tggtggagga gagtgggtct tgcaacaaag ttgcattttg ctagagacag gttaattgaa    1560
agcttttact gggcagttgg agttgcattt gaacctcaat acagtgattg tagaaattcc    1620
gtagcaaaaa tgttttcttt tgtaacaatc attgatgata tctatgatgt ttatggtact    1680
ctggatgagt tggagctatt tacagatgct gttgagagat gggatgttaa tgccatcgat    1740
gatcttcctg attatatgaa gctttgtttc ctagctcttt ataacactat caatgagata    1800
gcttatgata atctgaagga caaggggaa aacattcttc catacctaac aaaagcatgg    1860
gcagatttat gtaatgcatt cctacaagaa gcaaaatggt tgtacaataa gtccacacca    1920
acatttgatg aatatttcgg aaatgcatgg aaatcatcct cagggcctct tcaactagtt    1980
tttgcctact ttgccgttgt tcaaaacatc aagaaagagg aaattgataa cttacaaaag    2040
tatcatgata tcatcagtag gccttcccat atctttagac tttgtaacga cttggcttca    2100
gcatctgctg agatagcaag aggtgaaacc gcaaattctg tatcatgtta catgagaaca    2160
aaaggcattt ctgaggaact tgctactgaa tccgtaatga atttgatcga cgaaacctgg    2220
aaaaagatga caaagaaaa gcttggtggc tctctgtttg caaaaccttt tgttgaaaca    2280
gctattaacc ttgcaagaca atcccattgt acttatcata acggagatgc acatacttca    2340
ccagatgagc ttactaggaa aagagtactg tcagtaatca cagagcctat tctacctttt    2400
gagagataat aaaaataaga gttaccttaa atggtaactc ttattttttt aatgtcggta    2460
cc                                                                  2462

<210> SEQ ID NO 26
<211> LENGTH: 29
<212> TYPE: DNA
<213> ORGANISM: Artificial
<220> FEATURE:
<223> OTHER INFORMATION: Oligonucleotide primer for PCR

<400> SEQUENCE: 26
agccatggca ttgacacaaa tggcattag                                      29

<210> SEQ ID NO 27
<211> LENGTH: 32
<212> TYPE: DNA
<213> ORGANISM: Artificial
<220> FEATURE:
<223> OTHER INFORMATION: Oligonucleotide primer for PCR

<400> SEQUENCE: 27
tcggatcctt atctctcaaa gggtagaata gg                                  32

<210> SEQ ID NO 28
<211> LENGTH: 32
<212> TYPE: DNA
<213> ORGANISM: Artificial
<220> FEATURE:
<223> OTHER INFORMATION: Oligonucleotide primer for PCR

<400> SEQUENCE: 28
tcggatcctt acagagcgtt tttgatgatt tg                                  32
```